United States Patent
Shioda et al.

(10) Patent No.: US 11,555,035 B2
(45) Date of Patent: Jan. 17, 2023

(54) HETEROCYCLIC COMPOUND AND HARMFUL ARTHROPOD-CONTROLLING AGENT CONTAINING SAME

(71) Applicant: SUMITOMO CHEMICAL COMPANY, LIMITED, Chuo-ku (JP)

(72) Inventors: Takayuki Shioda, Takarazuka (JP); Yusuke Namba, Takarazuka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 113 days.

(21) Appl. No.: 16/955,971

(22) PCT Filed: Dec. 21, 2018

(86) PCT No.: PCT/JP2018/047143
§ 371 (c)(1),
(2) Date: Jun. 19, 2020

(87) PCT Pub. No.: WO2019/124529
PCT Pub. Date: Jun. 27, 2019

(65) Prior Publication Data
US 2021/0070753 A1    Mar. 11, 2021

(30) Foreign Application Priority Data
Dec. 22, 2017 (JP) .............................. JP2017-245957

(51) Int. Cl.
*C07D 471/04* (2006.01)
*A01N 43/90* (2006.01)

(52) U.S. Cl.
CPC ........... *C07D 471/04* (2013.01); *A01N 43/90* (2013.01)

(58) Field of Classification Search
CPC ....... C07D 471/04; A01N 43/90; A01N 25/00
See application file for complete search history.

(56) References Cited

U.S. PATENT DOCUMENTS

| | | | |
|---|---|---|---|
| 9,403,771 B2 * | 8/2016 | Takahashi | ............ C07D 513/04 |
| 2014/0194290 A1 | 7/2014 | Takahashi et al. | |
| 2017/0240554 A1 | 8/2017 | Edmunds et al. | |
| 2017/0267672 A1 | 9/2017 | Stoller et al. | |

FOREIGN PATENT DOCUMENTS

| | | |
|---|---|---|
| CN | 101128452 A | 2/2008 |
| CN | 101490037 A | 7/2009 |
| CN | 103717598 A | 4/2014 |
| CN | 104394694 A | 3/2015 |
| CN | 104331164 A | 10/2015 |
| CN | 106604922 A | 4/2017 |
| CN | 106795167 A | 5/2017 |
| EP | 2 865 266 A1 | 4/2015 |
| JP | 2014-111558 A | 6/2014 |
| JP | 2017-526678 A | 9/2017 |
| WO | WO 2006/080821 A1 | 8/2006 |
| WO | WO 2008/007900 A1 | 1/2008 |
| WO | WO 2013/018928 A1 | 2/2013 |
| WO | WO 2014/125651 A1 | 8/2014 |
| WO | WO 2016/002594 A1 | 1/2016 |
| WO | WO 2016-030229 A1 | 3/2016 |
| WO | WO 2016/046071 A1 | 3/2016 |
| WO | WO 2016/059145 A1 | 4/2016 |
| WO | WO 2018/091389 A1 | 5/2018 |

OTHER PUBLICATIONS

Patani, G.A. et al. "Bioisosterism: A Rational Approach in Drug Design" Chem. Rev. 1996, 96, 3147-3176 (Year: 1996).*
Combined Chinese Office Action and Search Report dated Jul. 20, 2021 in Chinese Patent Application No. 201880082367.9 (with English translation), 16 pages.
Extended European Search Report dated Jul. 5, 2021 in corresponding European Patent Application No. 18891186.1, 10 pages.
Indian Office Action dated Sep. 15, 2021 in Indian Patent Application No. 202047026553 (with English translation), 5 pages.
English translation of the International Search Report dated Mar. 5, 2019 in PCT/JP2018/047143, 2 pages.
English translation of the International Preliminary Report on Patentability and Written Opinion of the International Searching Authority dated Jun. 23, 2020 in PCT/JP2018/047143, 5 pages.

* cited by examiner

*Primary Examiner* — Andrew S Rosenthal
(74) *Attorney, Agent, or Firm* — Oblon, McClelland, Maier & Neustadt, L.L.P.

(57) ABSTRACT

The present invention provides a compound having an excellent control effect on a harmful arthropod. A compound represented by formula (I)

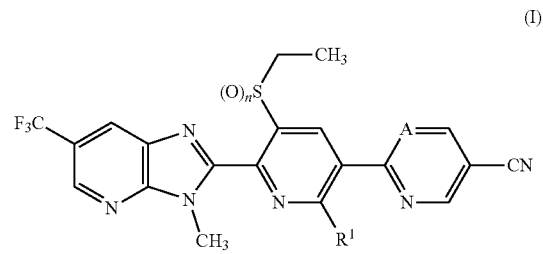

[wherein:
  A represents a CH or a nitrogen atom;
  $R^1$ represents a hydrogen atom or a $NR^2R^3$;
  $R^2$ and $R^3$ are identical to or different from each other, and each represent a C1-C6 alkyl group, a hydrogen atom, or the like; and
  n represents 0, 1, or 2]
has an excellent control effect on a harmful arthropod.

12 Claims, No Drawings

HETEROCYCLIC COMPOUND AND HARMFUL ARTHROPOD-CONTROLLING AGENT CONTAINING SAME

CROSS-REFERENCE TO RELATED APPLICATIONS

The present application is a 35 U.S.C. § 371 national stage patent application of International patent application PCT/JP2018/047143, filed on Dec. 21, 2018, which is based on and claims the benefits of priority to Japanese Application No. 2017-245957, filed on Dec. 22, 2017. The entire contents of these applications are incorporated herein by reference.

TECHNICAL FIELD

This application claims the priority to and the benefit of Japanese Patent Application No. 2017-245957 filed on Dec. 22, 2017, the entire contents of which are incorporated herein by reference.

The present invention relates to heterocyclic compounds and agents for controlling harmful arthropods comprising the same.

BACKGROUND ART

To date, various compounds have been studied in order to control harmful arthropods. For example, Patent Document 1 discloses that certain kinds of compound have control effects on harmful arthropods.

CITATION LIST

Patent Document

Patent Document 1: WO 2013/018928 pamphlet

SUMMARY OF THE INVENTION

Problems to be Solved by Invention

An object of the present invention is to provide compounds having excellent control efficacy against harmful arthropods.

Means to Solve Problems

The present invention provides the followings.
[1] A compound represented by formula (I)

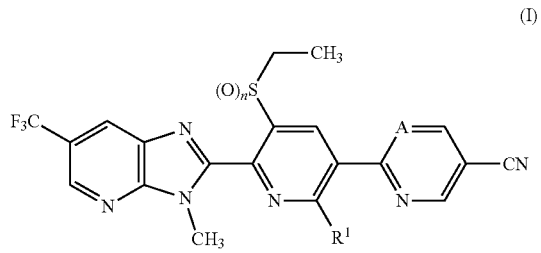

(I)

[wherein:
A represents a CH or a nitrogen atom;
$R^1$ represents a hydrogen atom or a $NR^2R^3$;
$R^2$ and $R^3$ are identical to or different from each other, and each represent a C1-C6 alkyl group optionally having one or more halogen atom(s) or a hydrogen atom; and
n represents 0, 1, or 2]
(hereinafter referred to as "Present compound" or "compound of the present invention").

[2] The compound according to [1], wherein $R^1$ represents a hydrogen atom.

[3] A composition for controlling a harmful arthropod comprising the compound according to [1] or [2] and an inert carrier.

[4] A method for controlling a harmful arthropod which comprises applying an effective amount of the compound according to [1] or [2] to a harmful arthropod or a habitat where a harmful arthropod lives.

[5] A composition comprising one or more ingredient(s) selected from the group consisting of Group (a) and Group (b), and the compound according to [1] or [2]:
Group (a): a group consisting of insecticidal active ingredients, miticidal active ingredients, and nematicidal active ingredients;
Group (b): fungicidal active ingredients.

[6] A method for controlling a harmful arthropod which comprises applying an effective amount of the composition according to [5] to a harmful arthropod or a habitat where a harmful arthropod lives.

[7] A seed or a vegetative reproduction organ holding an effective amount of the compound according to [1] or [2] or an effective amount of the composition according to [5].

Effect of Invention

According to the present invention, harmful arthropods can be controlled.

MODE FOR CARRYING OUT THE INVENTION

The substituents in the present invention are explained as follows.

The term of "halogen atom" represents a fluorine atom, a chlorine atom, a bromine atom, or an iodine atom.

When a substituent has two or more halogen atoms, these halogen atoms may be identical to or different from each other.

Examples of the C1-C6 alkyl group optionally having one or more halogen atom(s) include a methyl group, an ethyl group, a propyl group, an isopropyl group, a 1,1-dimethylpropyl group, a 1,2-dimethylpropyl group, a butyl group, a tert-butyl group, a pentyl group, a hexyl group, a trifluoromethyl group, a 2,2,2-trifluoroethyl group, a 4-chlorobutyl group, and a 4-bromo-1-(trifluoromethyl)pentyl group.

Embodiments of the Present compound include the following compounds.

Embodiment 1

The Present compound, wherein $R^1$ represents a hydrogen atom.

Embodiment 2

The Present compound, wherein $R^1$ represents a $NR^2R^3$.

Embodiment 3

The Present compound, wherein $R^1$ represents an amino group.

Embodiment 4

The Present compound, wherein $R^1$ represents a hydrogen atom or an amino group.

Embodiment 5

The Present compound, wherein $R^1$ represents a hydrogen atom, an amino group, or a methylamino group.

Embodiment 6

The Present compound, wherein A represents a CH.

Embodiment 7

The Present compound, wherein A represents a nitrogen atom.

Embodiment 8

The Present compound, wherein n represents 2.

Embodiment 9

The compound according to any one of Embodiments 1 to 5, wherein A represents a CH and n represents 2.

Embodiment 10

The compound according to any one of Embodiments 1 to 5, wherein A represents a nitrogen atom and n represents 2.

The Present compound may be mixed with an acid such as hydrochloric acid, sulfuric acid, nitric acid, phosphoric acid, sulfonic acid, acetic acid, and benzoic acid to form an acid addition salt such as hydrochloride, sulfate, nitrate, phosphate, sulfonate, acetate, and benzoate.

Process 1

The Present compound may be prepared by reacting a compound represented by formula (M-1) (hereinafter referred to as "Compound (M-1)") with a compound represented by formula (M-2) (hereinafter referred to as "Compound (M-2)") in the presence of a base and a catalyst.

[wherein $X^1$ represents a chlorine atom, a bromine atom, or an iodine atom; and the other symbols are the same as defined above.]

The reaction is usually carried out in a solvent. Examples of the solvent to be used in the reaction include ethers such as tetrahydrofuran, 1,4-dioxane, ethylene glycol dimethyl ether, and methyl tert-butyl ether (hereinafter referred to as "MTBE") (hereinafter collectively referred to as "ethers"); aromatic hydrocarbons such as toluene and xylene; aprotic polar solvents such as N-methylpyrrolidone and dimethyl sulfoxide (hereinafter referred to as "DMSO") (hereinafter collectively referred to as "aprotic polar solvents"); halogenated hydrocarbons such as dichloromethane and chloroform (hereinafter collectively referred to as "halogenated hydrocarbons"); nitriles such as acetonitrile and isobutyronitrile (hereinafter collectively referred to as "nitriles"); water; and mixed solvents thereof.

Examples of the base to be used in the reaction include organic bases such as triethylamine, diisopropylethylamine, pyridine, and 4-(dimethylamino)pyridine (hereinafter collectively referred to as "organic bases"); alkali metal carbonates such as sodium carbonate and potassium carbonate (hereinafter collectively referred to as "alkali metal carbonates"); alkali metal hydroxides such as sodium hydroxide and potassium hydroxide; alkali metal fluorides such as sodium fluoride, potassium fluoride, and cesium fluoride; and alkali metal phosphates such as tripotassium phosphate.

Examples of the catalyst to be used in the reaction include palladium(II) acetate, dichlorobis(triphenylphosphine)palladium(II), and bis(diphenylphosphaneferrocenyl)palladium(II) dichloride.

In the reaction, the Compound (M-2) is usually used at a ratio of 1 to 10 mol, the base is usually used at a ratio of 1 to 10 mol, and the catalyst is usually used at a ratio of 0.0001 to 1 mol, relative to 1 mol of the Compound (M-1).

The reaction temperature is usually within the range of 0° C. to 150° C. The reaction time is usually within the range of 0.1 to 24 hour(s).

When the reaction is completed, the reaction mixture may be subjected to a work-up such as adding water to the reaction mixture, extracting the resulting reaction mixture

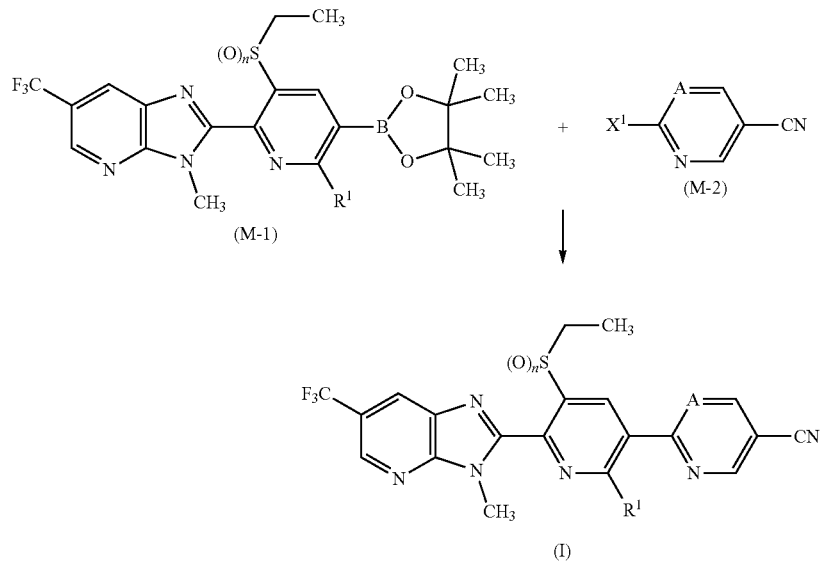

with organic solvent(s), and drying or concentrating the resulting organic layer to give the Present compound.

The Compound (M-2) may be a known compound, or may be prepared according to known method(s).

Process 2

A compound represented by formula (I-c) (hereinafter referred to as "Compound (I-c)") may be prepared by reacting a compound represented by formula (I-a) (hereinafter referred to as "Compound (I-a)") or a compound represented by formula (I-b) (hereinafter referred to as "Compound (I-b)") with an oxidizing agent. The Compound (I-b) may be prepared by reacting the Compound (I-a) with an oxidizing agent.

reaction mixture, extracting the resulting reaction mixture with organic solvent(s), washing the resulting organic layer with an aqueous solution of a reducing agent (for example, sodium sulfite or sodium thiosulfate) and an aqueous solution of a base (for example, sodium hydrogen carbonate) as needed, and drying or concentrating the resulting organic layer to give the Compound (I-b).

Next, a method for producing the Compound (I-c) from the Compound (I-b) is described.

The reaction is usually carried out in a solvent. Examples of the solvent to be used in the reaction include halogenated hydrocarbons, nitriles, alcohols, acetic acid, water, and mixed solvents thereof.

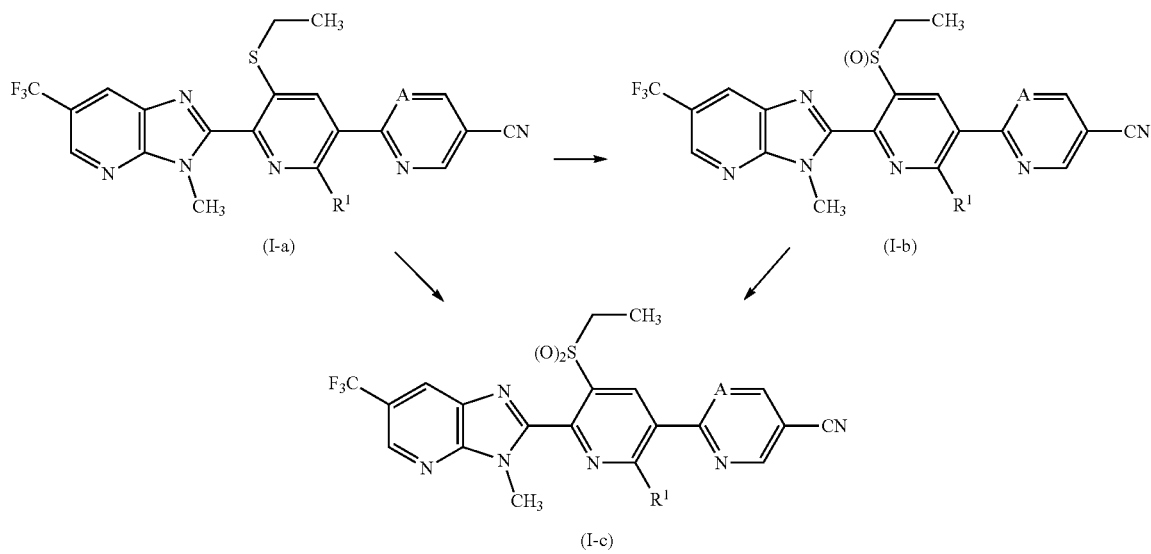

[wherein the symbols are the same as defined above.]

First, a method for producing the Compound (I-b) from the Compound (I-a) is described.

The reaction is usually carried out in a solvent. Examples of the solvent to be used in the reaction include halogenated hydrocarbons; nitriles; alcohols such as methanol and ethanol (hereinafter collectively referred to as "alcohols"); acetic acid; water; and mixed solvents thereof.

Examples of the oxidizing agent to be used in the reaction include sodium periodate, m-chloroperbenzoic acid (hereinafter referred to as "mCPBA"), and hydrogen peroxide.

When hydrogen peroxide is used as the oxidizing agent, a base or a catalyst may be added to the reaction as needed.

Examples of the base include sodium carbonate.

Examples of the catalyst include tungstic acid and sodium tungstate.

In the reaction, the oxidizing agent is usually used at a ratio of 1 to 1.2 mol, relative to 1 mol of the Compound (I-a).

When a base is used in the reaction, the base is usually used at a ratio of 0.01 to 1 mol, relative to 1 mol of the Compound (I-a).

When a catalyst is used in the reaction, the catalyst is usually used at a ratio of 0.01 to 0.5 mol, relative to 1 mol of the Compound (I-a).

The reaction temperature is usually within the range of −20 to 80° C. The reaction time is usually within the range of 0.1 to 12 hour(s).

When the reaction is completed, the reaction mixture may be subjected to a work-up such as adding water to the Examples of the oxidizing agent to be used in the reaction include mCPBA and hydrogen peroxide.

When hydrogen peroxide is used as the oxidizing agent, a base or a catalyst may be added to the reaction as needed.

Examples of the base include sodium carbonate.

Examples of the catalyst include sodium tungstate.

In the reaction, the oxidizing agent is usually used at a ratio of 1 to 2 mol, relative to 1 mol of the Compound (I-b).

When a base is used in the reaction, the base is usually used at a ratio of 0.01 to 1 mol, relative to 1 mol of the Compound (I-b).

When a catalyst is used in the reaction, the catalyst is usually used at a ratio of 0.01 to 0.5 mol, relative to 1 mol of the Compound (I-b).

The reaction temperature is usually within the range of −20 to 120° C. The reaction time is usually within the range of 0.1 to 12 hour(s).

When the reaction is completed, the reaction mixture may be subjected to a work-up such as adding water to the reaction mixture, extracting the resulting reaction mixture with organic solvent(s), washing the resulting organic layer with an aqueous solution of a reducing agent (for example, sodium sulfite or sodium thiosulfate) and an aqueous solution of a base (for example, sodium hydrogen carbonate) as needed, and drying or concentrating the resulting organic layer to give the Compound (I-c).

Also, the Compound (I-c) may be prepared in one step reaction (one-pot) by reacting the Compound (I-a) with an oxidizing agent.

The reaction may be carried out according to the same method as the method for producing the Compound (I-c) from the Compound (I-b) by usually using an oxidizing agent at a ratio of 2 to 5 mol relative to 1 mol of the Compound (I-a).

Process 3

A compound represented by formula (I-d) (hereinafter referred to as "Compound (I-d)") may be prepared by reacting a compound represented by formula (M-3-a) (hereinafter referred to as "Compound (M-3-a)") with an acid.

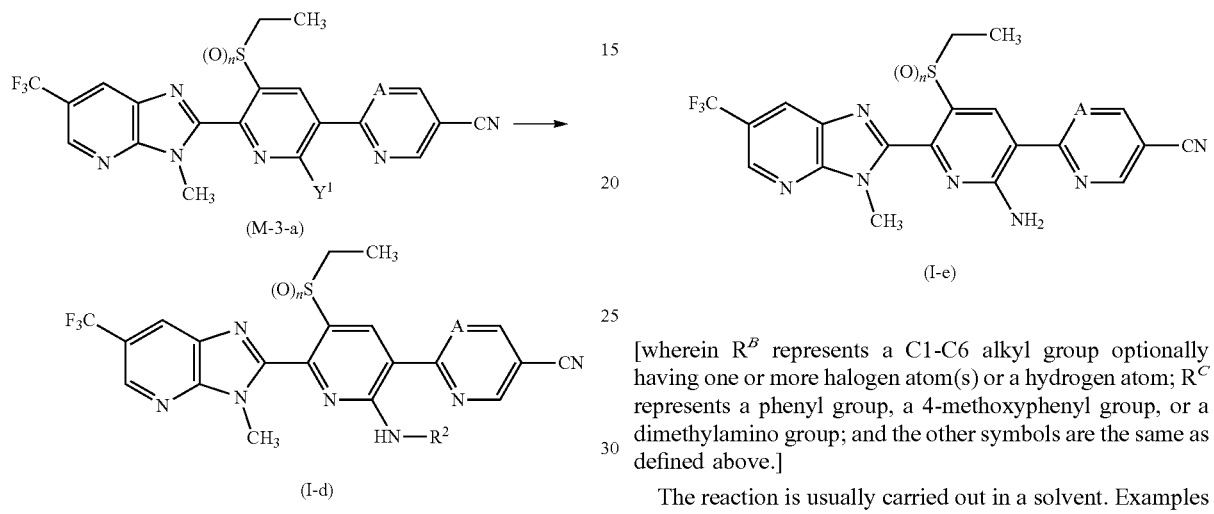

[wherein $Y^1$ represents a $NR^2C(O)R^4$ or a $NR^2C(O)OR^4$; $R^4$ represents a C1-C6 alkyl group optionally having one or more halogen atom(s); and the other symbols are the same as defined above.]

The reaction is usually carried out in a solvent. Examples of the solvent to be used in the reaction include ethers, halogenated hydrocarbons, aprotic polar solvents, and mixed solvents thereof.

Examples of the acid to be used in the reaction include sulfonic acids such as para-toluenesulfonic acid (hereinafter collectively referred to as "sulfonic acids"); carboxylic acids such as trifluoroacetic acid (hereinafter collectively referred to as "carboxylic acids"); and mineral acids such as hydrogen chloride and sulfuric acid (hereinafter collectively referred to as "mineral acids").

In the reaction, the acid is usually used at a ratio of 0.1 to 5 mol, relative to 1 mol of the Compound (M-3-a).

The reaction temperature is usually within the range of 0 to 200° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to isolate the Compound (I-d).

Process 4

A compound represented by formula (I-e) (hereinafter referred to as "Compound (I-e)") may be prepared by reacting a compound represented by formula (M-3-b) (hereinafter referred to as "Compound (M-3-b)") with an acid.

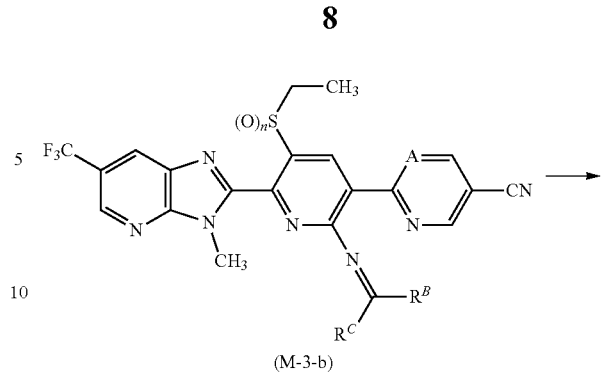

[wherein $R^B$ represents a C1-C6 alkyl group optionally having one or more halogen atom(s) or a hydrogen atom; $R^C$ represents a phenyl group, a 4-methoxyphenyl group, or a dimethylamino group; and the other symbols are the same as defined above.]

The reaction is usually carried out in a solvent. Examples of the solvent to be used in the reaction include ethers, halogenated hydrocarbons, aprotic polar solvents, and mixed solvents thereof.

Examples of the acid to be used in the reaction include sulfonic acids; carboxylic acids; and mineral acids.

In the reaction, the acid is usually used at a ratio of 0.1 to 5 mol, relative to 1 mol of the Compound (M-3-b).

The reaction temperature is usually within the range of 0 to 200° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to isolate the Compound (I-e).

Reference Process 1

The Compound (M-1) may be prepared by reacting a compound represented by formula (M-4) (hereinafter referred to as "Compound (M-4)") with bis(pinacolato)diboron in the presence of a palladium catalyst and a base.

-continued

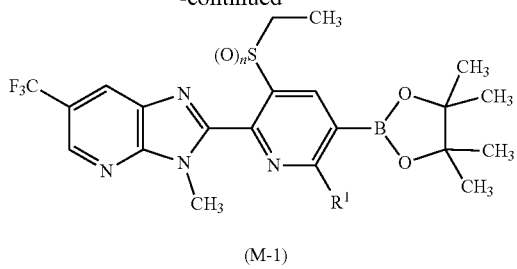

(M-1)

[wherein the symbols are the same as defined above.]

The reaction may be carried out according to the same method as described in Chem. Rev., 1995, 95, 2457.

Reference Process 2

A compound represented by formula (M-4-a) (hereinafter referred to as "Compound (M-4-a)") may be prepared by reacting a compound represented by formula (M-5) (hereinafter referred to as "Compound (M-5)") with a halogenating agent.

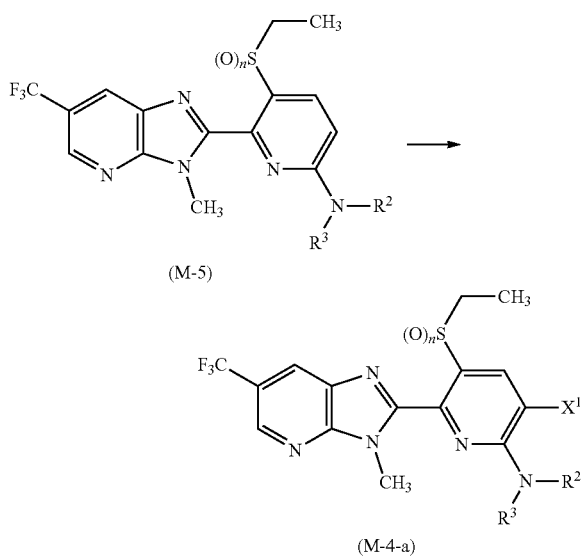

[wherein the symbols are the same as defined above.]

The reaction is usually carried out in a solvent. Examples of the solvent to be used in the reaction include ethers, halogenated hydrocarbons, nitriles, water, and mixed solvents thereof.

Examples of the halogenating agent to be used in the reaction include N-chlorosuccinimide, N-bromosuccinimide, N-iodosuccinimide, bromine, and iodine.

In the reaction, the halogenating agent is usually used at a ratio of 1 to 5 mol, relative to 1 mol of the Compound (M-5).

The reaction temperature is usually within the range of −10 to 100° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to isolate the Compound (M-4-a).

The Compound (M-5) may be prepared according to the same method as described in WO 2017/077968 pamphlet.

Reference Process 3

A compound represented by formula (M-7-a) (hereinafter referred to as "Compound (M-7-a)") may be prepared by reacting a compound represented by formula (M-4-b) (hereinafter referred to as "Compound (M-4-b)") with a compound represented by formula (M-6) (hereinafter referred to as "Compound (M-6)").

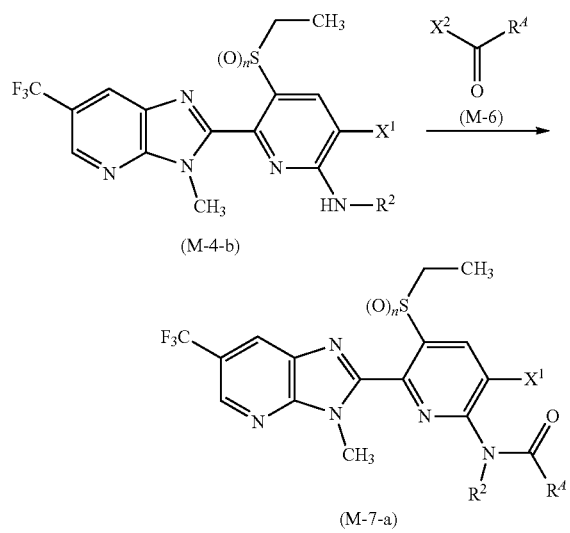

[wherein $X^2$ represents a chlorine atom or a $OC(O)R^4$; and the other symbols are the same as defined above.]

The reaction is usually carried out in a solvent. Examples of the solvent to be used in the reaction include ethers; hydrocarbons such as hexane and toluene (hereinafter collectively referred to as "hydrocarbons"); halogenated hydrocarbons; nitriles; aprotic polar solvents; and mixed solvents thereof.

In the reaction, a base may be used as needed. Examples of the base to be used in the reaction include organic bases and alkali metal carbonates.

In the reaction, the Compound (M-6) is usually used at a ratio of 1 to 1.5 mol, relative to 1 mol of the Compound (M-4-b).

When a base is used in the reaction, the base is usually used at a ratio of 1 to 5 mol, relative to 1 mol of the Compound (M-4-b).

The reaction temperature is usually within the range of 0 to 120° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to isolate the Compound (M-7-a).

The Compound (M-6) may be a known compound, or may be prepared according to known method(s).

Reference Process 4

A compound represented by formula (M-7-b) (hereinafter referred to as "Compound (M-7-b)") may be prepared by reacting the Compound (M-4-b) with a compound represented by formula (M-8) (hereinafter referred to as "Compound (M-8)")

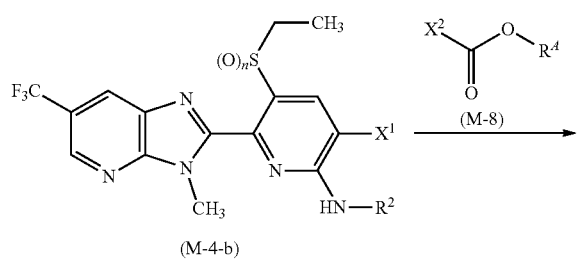

(M-4-b)

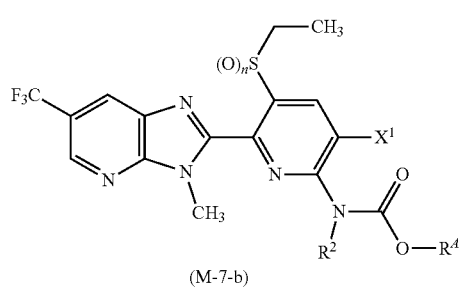

(M-7-b)

[wherein the symbols are the same as defined above.]

The reaction may be carried out according to the same method as the Reference process 3.

The Compound (M-8) may be a known compound, or may be prepared according to known method(s).

Reference Process 5

A compound represented by formula (M-7-c) (hereinafter referred to as "Compound (M-7-c)") may be prepared by reacting a compound represented by formula (M-4-c) (hereinafter referred to as "Compound (M-4-c)") with a compound represented by formula (M-9) (hereinafter referred to as "Compound (M-9)").

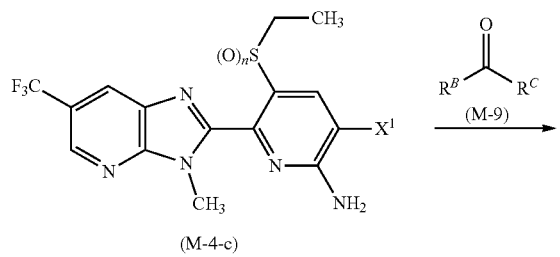

(M-4-c)

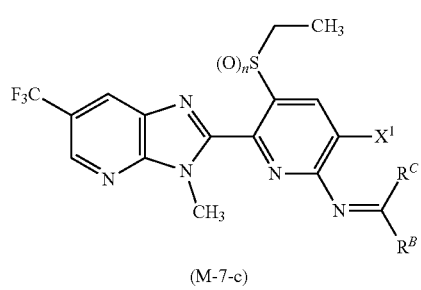

(M-7-c)

[wherein the symbols are the same as defined above.]

The reaction is usually carried out in a solvent. Examples of the solvent to be used in the reaction include ethers, hydrocarbons, halogenated hydrocarbons, nitriles, aprotic polar solvents, and mixed solvents thereof. Also, the Compound (M-9) may also be used as a solvent.

The reaction may also be carried out in the presence of an acid as needed.

Examples of the acid include sulfonic acids and mineral acids.

In the reaction, the Compound (M-9) is usually used at a ratio of 1 to 5 mol, relative to 1 mol of the Compound (M-4-c).

When an acid is used in the reaction, the acid is usually used at a ratio of 0.1 to 2 mol, relative to 1 mol of the Compound (M-4-c).

The reaction temperature is usually within the range of 0 to 150° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to isolate the Compound (M-7-c).

The Compound (M-9) may be a known compound, or may be prepared according to known method(s).

Reference Process 6

A compound represented by formula (M-10) (hereinafter referred to as "Compound (M-10)") may be prepared by reacting a compound represented by formula (M-7) (hereinafter referred to as "Compound (M-7)") with bis(pinacolato)diboron in the presence of a palladium catalyst and a base.

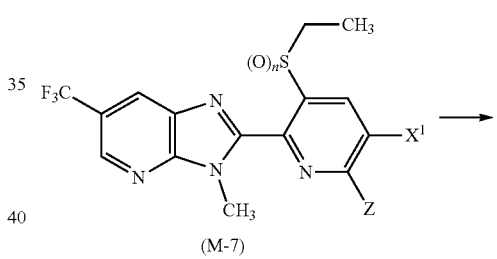

(M-7)

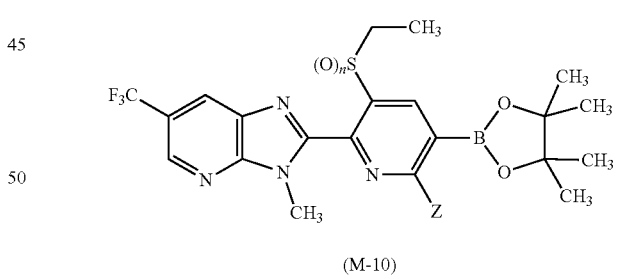

(M-10)

[wherein Z represents a $NR^2C(O)R^A$, a $NR^2C(O)OR^A$, or a $N=CR^BR^C$; and the other symbols are the same as defined above.]

These reactions may be carried out according to the same method as the Reference process 1.

Reference Process 7

A compound represented by formula (M-3) (hereinafter referred to as "Compound (M-3)") may be prepared by reacting a compound represented by formula (M-10) (hereinafter referred to as "Compound (M-10)") with the Compound (M-2) in the presence of a base and a catalyst.

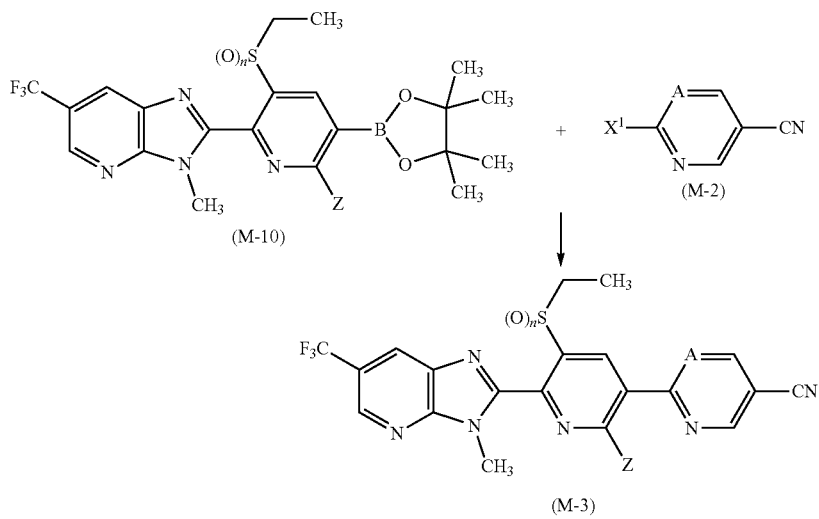

[wherein the symbols are the same as defined above.]

The reaction may be carried out according to the same method as the Process 1.

The Present compound may be mixed with or used in combination with one or more ingredient(s) selected from the group consisting of the following Group (a), Group (b), Group (c), Group (d), Group (e), Group (f), Group (g), and Group (h) (hereinafter collectively referred to as "Present ingredient").

When the Present compound is mixed with or used in combination with the Present ingredient, they are used simultaneously, separately, or at time intervals with each other.

When the Present compound is used simultaneously with the Present ingredient, the Present compound and the Present ingredient may be contained in separate formulations or contained in one formulation.

One aspect of the present invention provides a composition comprising one or more ingredient(s) selected from the group consisting of Group (a) and Group (b), and the Present compound (hereinafter referred to as "Composition X").

Group (a) is a group consisting of each active ingredient of acetylcholinesterase inhibitors (for example, carbamate insecticides and organophosphorus insecticides), GABAergic chloride channel antagonists (for example, phenylpyrazole insecticides), sodium channel modulators (for example, pyrethroid insecticides), nicotinic acetylcholine receptor competitive modulators (for example, neonicotinoid insecticides), nicotinic acetylcholine receptor allosteric modulators, glutamatergic chloride channel allosteric modulators (for example, macrolide insecticides), juvenile hormone mimics, multisite inhibitors, chordotonal organ TRPV channel modulators, mites growth inhibitors, mitochondrial ATP biosynthetic enzyme inhibitors, oxidative phosphorylation uncouplers, nicotinic acetylcholine receptor channel blockers (for example, nereistoxin insecticides), chitin synthesis inhibitors, molting inhibitors, ecdysone receptor agonists, octopamine receptor agonists, mitochondrial electron transport system complex I, II, III, and IV inhibitors, voltage-dependent sodium channel blockers, acetyl CoA carboxylase inhibitors, ryanodine receptor modulators (for example, diamide insecticides), chordotonal organmodulators, and microbial insecticides, and other insecticidal active ingredients, miticidal active ingredients, and nematicidal active ingredients. These ingredients are described in the classification on the basis of action mechanism by IRAC.

Group (b) is a group consisting of nucleic acid synthesis inhibitors (for example, phenylamide fungicides and acylamino acid fungicides), cell division and cytoskeleton inhibitors (for example, MBC fungicides), respiration inhibitors (for example, QoI fungicides and QiI fungicides), amino acid synthesis and protein synthesis inhibitors (for example, anilinopyridine fungicides), signaling inhibitors, lipid synthesis and membrane synthesis inhibitors, sterol biosynthesis inhibitors (for example, DMI fungicides such as triazole fungicides), cell-wall synthesis inhibitors, melanin synthesis inhibitors, plant defense inducers, fungicides with multi-site contact activity, microbial fungicides, and other fungicidal active ingredients. These ingredients are described in the classification on the basis of action mechanism by FRAC.

Group (c) is a group of plant growth regulatory ingredients (including mycorrhizal fungi and root nodule bacteria).

Group (d) is a group of phytotoxicity-reducing ingredients.

Group (e) is a group of synergists.

Group (f) is a group of repellent ingredients consisting of bird repellent ingredients, insect repellent ingredients, and animal repellent ingredients.

Group (g) is a group of molluscicidal ingredients.

Group (h) is a group of insect pheromones.

Hereinafter, examples of the combination of the Present ingredient and the Present compound are described. For example, alanycarb+SX indicates a combination of alanycarb and SX.

The abbreviation of "SX" indicates any one of the Present compounds selected from the Compound groups SX1 to SX6 described in Examples. Also, all of the following Present ingredients are known ingredients, and may be obtained from commercially available formulations, or may be prepared by known methods. When the Present ingredient is a microorganism, it may also be available from a bacterial authority depository. Further, the number in parentheses represents the CAS RN (registered trademark).

Combinations of the Present ingredient in the above Group (a) and the Present compound:

abamectin+SX, acephate+SX, acequinocyl+SX, acetamiprid+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, bark of *Celastrus angulatus*+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium cyanide+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, coumaphos+SX, cryolite+SX, cyanophos+SX, cyantraniliprole+SX, cycloniliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dinotefuran+SX, disodium octaborate+SX, disulfoton+SX, DNOC (2-methyl-4,6-dinitrophenol)+SX, doramectin+SX, dried leaves of *Dryopteris filix-mas*+SX, emamectin-benzoate+SX, empenthrin+SX, endosulfan+SX, EPN (O-ethyl O-(4-nitrophenyl) phenylphosphonothioate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absinthium*+SX, extract of *Cassia nigricans*+SX, extract of *Clitoria ternatea*+SX, extract of *Symphytum officinale*+SX, extracts or simulated blend of *Chenopodium ambrosioides*+SX, extract of *Tanacetum vulgare*+SX, extract of *Urtica dioica*+SX, extract of *Viscum album*+SX, famphur+SX, fenamiphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, flucycloxuron+SX, flucythrinate+SX, fluensulfone+SX, flufenoprox+SX, flufenoxuron+SX, flufiprole+SX, flumethrin+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalothrin+SX, GS-omega/kappa HXTX-Hvla peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SX, hydroprene+SX, imicyafos+SX, imidacloprid+SX, imiprothrin+SX, indoxacarb+SX, isofenphos+SX, isoprocarb+SX, isopropyl-O-(methoxyaminothiophosphoryl)salicylate+SX, isoxathion+SX, ivermectin+SX, kadethrin+SX, kappa-tefluthrin+SX, kappa-bifenthrin+SX, kinoprene+SX, lambda-cyhalothrin+SX, lepimectin+SX, lime sulfur+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methylbromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, neem oil+SX, nicotine+SX, nicotine-sulfate+SX, nitenpyram+SX, novaluron+SX, noviflumuron+SX, oil of the seeds of *Chenopodium anthelminticum*+SX, omethoate+SX, oxamyl+SX, oxazosulfyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, potassium cyanide+SX, prallethrin+SX, profenofos+SX, profluthrin+SX, propargite+SX, propetamphos+SX, propoxur+SX, propylene glycol alginate+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, selamectin+SX, sigma-cypermethrin+SX, silafluofen+SX, sodium borate+SX, sodium cyanide+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, terpene constituents of the extract of *Chenopodium ambrosioides* near *ambrosioides* (Brand name: Terpenoid blend QRD 460)+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, wood extract of *Quassia amara*+SX, XMC (3,5-dimethylphenyl N-methylcarbamate)+SX, xylylcarb+SX, zeta-cypermethrin+SX, zinc phosphide+SX, 3-bromo-N-[2,4-dichloro-6-(methylcarbamoyl)phenyl]-1-(3,5-dichloropyridin-2-yl)-1H-pyrazole-5-carboxamide (1104384-14-6)+SX, N-[3-chloro-1-(pyridin-3-yl)-1H-pyrazol-4-yl]-N-ethyl-3-(3,3,3-trifluoropropanesulfinyl)propaneamide (1477923-37-7)+SX, 4-[5-(3,5-dichlorophenyl)-5-(trifluoromethyl)-4,5-dihydro-1,2-oxazol-3-yl]-2-methyl-N-(1-oxothietan-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propaneamide (1118626-57-5)+SX, N-[2-bromo-6-chloro-4-(1,1,1,2,3,3,3-heptafluoropropan-2-yl)phenyl]-3-{ethyl[(pyridin-4-yl)carbonyl]amino}-2-methoxybenzamide (1429513-53-0)+SX, N-[2-bromo-6-chloro-4-(1,1,1,2,3,3,3-heptafluoropropan-2-yl)phenyl]-3-[ethyl(4-cyanobenzoyl)amino]-2-methoxybenzamide (1609007-65-9)+SX, N-[2-bromo-6-difluoromethoxy-4-(1,1,1,2,3,3,3-heptafluoropropan-2-yl)phenyl]-3-{methyl[(pyridin-4-yl)carbonyl]amino}-2-methoxybenzamide (1630969-78-6)+SX, 1-{2-fluoro-4-methyl-5-[(2,2,2-trifluoroethyl)sulfinyl]phenyl}-3-(trifluoromethyl)-1H-1,2,4-triazole-5-amine (885026-50-6)+SX, BT crop protein Cry1Ab+SX, BT crop protein Cry1Ac+SX, BT crop protein Cry1Fa+SX, BT crop protein Cry1A.105+SX, BT crop protein Cry2Ab+SX, BT crop protein Vip3A+SX, BT crop protein Cry3A+SX, BT crop protein Cry3Ab+SX, BT crop protein Cry3Bb+SX, BT crop protein Cry34Ab1/Cry35Ab1+SX, *Adoxophyes orana* granulosis virus BV-0001+SX, *Anticarsia gemmatalis* mNPV+SX, *Autographa californica* mNPV+SX, *Cydia pomonella* GV V15+SX, *Cydia pomonella* GV V22+SX, *Cryptophlebia leucotreta* GV+SX, *Dendrolimus punctatus* cypovirus+SX, *Helicoverpa armigera* NPV BV-0003+SX, *Helicoverpa zea* NPV+SX, *Lymantria dispar* NPV+SX, *Mamestra brassicae* NPV+SX, *Mamestra configurata* NPV+SX, *Neodiprion abietis* NPV+SX, *Neodiprion lecontei* NPV+SX, *Neodiprion sertifer* NPV+SX, *Nosema locustae*+SX, *Orgyia pseudotsugata* NPV+SX, *Pieris rapae* GV+SX, *Plodia interpunctella* GV+SX, *Spodoptera exigua* mNPV+SX, *Spodoptera littoralis* mNPV+SX, *Spodoptera litura* NPV+SX, *Arthrobotrys dactyloides*+SX, *Bacillus firmus* GB-126+SX, *Bacillus firmus* 1-1582+SX, *Bacillus megaterium*+SX, *Bacillus* sp. AQ175+SX, *Bacillus* sp. AQ177+SX, *Bacillus* sp. AQ178+SX, *Bacillus sphaericus* 2362+SX, *Bacillus sphaericus* ABTS1743+SX, *Bacillus sphaericus* Serotype H5a5b+SX, *Bacillus thuringiensis* AQ52+SX, *Bacillus thuringiensis* BD#32+SX, *Bacillus thuringiensis* CR-371+SX, *Bacillus thuringiensis* subsp. *Aizawai* ABTS-1857+SX, *Bacillus thuringiensis* subsp. *Aizawai* AM65-52+SX, *Bacillus thuringiensis* subsp. *Aizawai* GC-91+SX, *Bacillus thuringiensis* subsp. *Aizawai* Serotype H-7+SX, *Bacillus thuringiensis* subsp. *Kurstaki* ABTS351+SX, *Bacillus thuringiensis* subsp. *Kurstaki* BMP123+SX, *Bacillus thuringiensis* subsp. *Kurstaki* EG234+SX, *Bacillus thuringiensis* subsp. *Kurstaki* EG7841+SX, *Bacillus thuringiensis* subsp. *Kurstaki* EVB113-19+SX, *Bacillus thuringiensis* subsp. *Kurstaki* F810+SX, *Bacillus thuringiensis* subsp. *Kurstaki* HD-1+SX, *Bacillus thuringiensis* subsp. *Kurstaki* PB54+SX, *Bacillus thuringiensis* subsp. *Kurstaki* SA-11+SX, *Bacillus thuringiensis* subsp. *Kurstaki* SA-12+SX, *Bacillus thuringiensis* subsp. *Tenebriosis* NB176+SX, *Bacillus thuringiensis* subsp. *Thuringiensis* MPPL002+SX, *Bacillus thuringiensis* subsp. *morrisoni*+SX, *Bacillus thuringiensis* var. *colmeri*+SX, *Bacillus thuringiensis* var. *darmstadiensis* 24-91+SX, *Bacillus thuringiensis* var. *dendrolimus*+SX, *Bacillus thuringiensis* var. *galleriae*+SX, *Bacillus thuringiensis* var. *israelensis* BMP144+SX, *Bacillus thuringiensis* var. *israelensis* serotype H-14+SX, *Bacillus thuringiensis* var. *japonensis buibui*+SX, *Bacillus thuringiensis* var. *san diego* M-7+SX, *Bacillus thuringiensis* var. 7216+SX, *Bacillus thuringiensis* var. *aegypti*+SX, *Bacillus thuringiensis* var. T36+SX, *Beauveria bassiana* ANT-03+SX, *Beauveria bassiana* ATCC74040+SX, *Beauveria bassiana* GHA+SX, *Beauveria brongniartii*+SX, *Burkholderia rinojensis* A396+SX, *Chromobacterium subtsugae* PRAA4-1T+SX, *Dactyllela ellipsospora*+SX, *Dectylaria thaumasia*+SX, *Hirsutella minnesotensis*+SX, *Hirsutella rhossiliensis*+SX, *Hirsutella thompsonii*+SX, *Lagenidium giganteum*+SX, *Lecanicillium lecanii* KV01+SX, *Lecanicillium lecanii* conidia of strain DAOM198499+SX, *Lecanicillium lecanii* conidia of strain DAOM216596+SX, *Metarhizium anisopliae* F52+SX, *Metarhizium anisopliae* var. *acridum*+SX, *Metarhizium flavoviride*+SX, *Monacrosporium phymatopagum*+SX, *Paecilomyces fumosoroseus* Apopka97+SX, *Paecilomyces lilacinus* 251+SX, *Paecilomyces tenuipes* T1+SX, *Paenibacillus popilliae*+SX, *Pasteuria nishizawae* Pn1+SX, *Pasteuria penetrans*+SX, *Pasteuria usgae*+SX, *Pasteuria thoynei*+SX, *Serratia entomophila*+SX, *Verticillium chlamydosporium*+SX, *Verticillium lecani* NCIM1312+SX, Albendazole+SX, Amoscanate+SX, Amprolium+SX, Antimon guluconate sodium+SX, Arecoline+SX, Arsenamide+SX, Atovaquone+SX, Benzamidine hydrochloride+SX, Bephenium+SX, Bithionol+SX, Bithionol sulfoxide+SX, Bitoscanate+SX, Bromofenofos+SX, Bromoxanide+SX, Brotianide+SX, Bunamidine+SX, Butamisole+SX, Cambendazole+SX, Clioxanide+SX, Clonazepam+SX, Clorsulon+SX, Closantel+SX, Cyclobendazole+SX, Derquantel+SX, Diclazuril+SX, Diamfenetide+SX, Diaveridine+SX, Diethylcarbamazine+SX, Diethylcarbamazine citrate+SX, Dimadectin+SX, Diminazene aceturate+SX, Dinitolmide+SX, Disophenol+SX, Ematine+SX, Emodepside+SX, Eprinomectin+SX, Epsiprantel+SX, Febantel+SX, Fenbendazole+SX, Flubendazole+SX, Furazolidone+SX, Glycarpiramide+SX, Hetolin+SX, Hexachlorophene+SX, Hycanthone+SX, Hygromycin B+SX, Imidocarb hydrochloride+SX, Iodide dithiazanine+SX, Kainic acid+SX, Kamala+SX, Latidectin+SX, Levamisole+SX, Lucanthone+SX, Makli+SX, Mebendazole+SX, Melarsomine+SX, Menichlopholan+SX, Methyridine+SX, Metronidazole+SX, Milbemycin D+SX, Miracil D+SX, Mirasan+SX, Monepantel+SX, Morantel+SX, Nicarbazine+SX, Niclosamide+SX, Niridazole+SX, Nitazoxanide+SX, Nitroscanate+SX, Nitroxynil+SX, Nemadectin+SX, Oltipraz+SX, Oxamniquine+SX, Oxantel+SX, Oxibendazole+SX, Oxfendazole+SX, Oxyclozanide+SX, Pamaquine+SX, Parbendazole+SX, Paromomycin+SX, Paromomycin II+SX, Phenothiazine+SX, Phthalofyne+SX, Praziquantel+SX, Piperazine+SX, Ponazuril+SX, Primaquine+SX, Pyrantel pamoate+SX, Pyrantel tartrate+SX, Pyrimethamine+SX, Pyrvinium chloride+SX, Pyrvinium Pamoate+SX, Quinacrine+SX, Rafoxanide+SX, Ronidazole+SX, α-santonin+SX, Sulfadiazine+SX, Suramin sodium+SX, Tetramisole+SX, Thenium closylate+SX, Thiacetarsamide sodium+SX, Tinidazole+SX, Toltrazuril+SX, Tribromsalan+SX, Triclabendazole+SX, lenoremycin+SX, concanamycin A+SX, acetoprole+SX, lotilaner+SX, sarolaner+SX, isocycloseram+SX, *Metarhizium anisopliae* var. *anisopliae* BIPESCO 5/F52+SX, *Lecanicillium muscarium* Ve6+SX, N-ethyl-5-methyl-1-(3-methylbutan-2-yl)-N-(pyridazin-4-yl)-1H-pyrazole-4-carboxamide (1403615-77-9)+SX.

Combinations of the Present ingredient in the above Group (b) and the Present compound:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthivalicarb-isopropyl+SX, benzovindiflupyr+SX, binapacryl+SX, biphenyl+SX, bitertanol+SX, bixafen+SX, blasticidin-S+SX, Bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chloroneb+SX, chlorothalonil+SX, chlozolinate+SX, colletochlorin B+SX, copper(II) acetate+SX, copper(II) hydroxide+SX, copper oxychloride+SX, copper(II) sulfate+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, dimethachlone+SX, dimethirimol+SX, dimethomorph+SX, dimoxystrobin+SX, diniconazole+SX, diniconazole-M+SX, dinocap+SX, dipotassium hydrogenphosphite+SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, extract from *Melaleuca alternifolia*+SX, extract from *Reynoutria sachalinensis*+SX, extract from the cotyledons of lupine plantlets ("BLAD")+SX, extract of *Allium sativum*+SX, extract of *Equisetum arvense*+SX, extract of *Tropaeolum majus*+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, florylpicoxamid+SX, fluazinam+SX, fludioxonil+SX, flufenoxystrobin+SX, fluindapyr+SX, flumorph+SX, fluopicolide+SX, fluopyram+SX, fluopimomide+SX, fluoroimide+SX, fluoxastrobin+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hymexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, isoflucypram+SX, isoprothiolane+SX, isopyrazam+SX, isotianil+SX, kasugamycin+SX, kresoxim-methyl+SX, laminarin+SX, leaves and bark of *Quercus*+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metconazole+SX, methasulfocarb+SX, metiram+SX, metominostrobin+SX, metrafenone+SX, metyltetraprole+SX, mineral oils+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyrapropoyne+SX, pyraziflumid+SX, pyrazophos+SX, pyribencarb+SX, pyributicarb+SX, pyridachlometyl+SX, pyrifenox+SX, pyrimethanil+SX, pyrimorph+SX, pyriofenone+SX, pyrisoxazole+SX, pyroquilon+SX, Quillaja extract+SX, quinconazole+SX, quinofumelin+SX, quinoxyfen+SX, quintozene+SX, Saponins of *Chenopodium quinoa*+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, 3-(difluoromethyl)-N-methoxy-1-methyl-N-[(1R)-1-methyl-2-(2,4,6-trichlorophenyl)ethyl]pyrazole-4-carboxamide (1639015-48-7)+SX, 3-(difluoromethyl)-N-methoxy-1-methyl-N-[(1S)-1-methyl-2-(2,4,6-trichlorophenyl)ethyl]pyrazole-4-carboxamide (1639015-49-8)+SX, 3-(difluoromethyl)-1-methyl-N-(1,1,3-trimethylindan-4-yl)pyrazole-4-carboxamide (141573-94-6)+SX, 3-(difluoromethyl)-N-[(3R)-7-fluoro-1,1,3-trimethylindan-4-yl]-1-methylpyrazole-4-carboxamide (1513466-73-3)+SX, N'-[4-({3-[(4-chlorophenyl)methyl]-1,2,4-thiadiazol-5-yl}oxy)-2,5-dimethylphenyl]-N-ethyl-N-methylmethanimidamide (1202-781-91-6)+SX, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl=methanesulfonate (1360819-11-9)+SX, 4-(2-bromo-4-fluorophenyl)-N-(2-chloro-6-fluorophenyl)-1,3-dimethyl-1H-pyrazole-5-amine (1362477-26-6)+SX, 2,2-dimethyl-9-fluoro-5-(quinolin-3-yl)-2,3-dihydrobenzo[f][1,4]oxazepine (1207749-50-5)+SX, 2-[6-(3-fluoro-4-methoxyphenyl)-5-methylpyridin-2-yl]quinazoline (1257056-97-5)+SX, 5-fluoro-2-[(4-methylphenyl)methoxy]-4-pyrimidineamine (1174376-25-0)+SX, 5-fluoro-4-imino-3-methyl-1-tosyl-3,4-dihydropyrimidin-2(1H)-one (1616664-98-2)+SX, N'-(2,5-dimethyl-4-phenoxyphenyl)-N-ethyl-N-methylmethanimidamide (1052688-31-9)+SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridine-2-amine (1446247-98-8)+SX, α-[3-(4-chloro-2-fluorophenyl)-5-(2,4-difluorophenyl)-4-isoxazolyl]-3-pyridinemethanol (1229605-96-2)+SX, (αS)-[3-(4-chloro-2-fluorophenyl)-5-(2,4-difluorophenyl)-4-isoxazolyl]-3-pyridinemethanol (1229606-46-5)+SX, (αR)-[3-(4-chloro-2-fluorophenyl)-5-(2,4-difluorophenyl)-4-isoxazolyl]-3-pyridinemethanol (1229606-02-3)+SX, 2-{[3-(2-chlorophenyl)-2-(2,4-difluorophenyl)oxiran-2-yl]methyl}-2,4-dihydro-3H-1,2,4-triazole-3-thione (1342260-19-8)+SX, 2-{[(2R,3S)-3-(2-chlorophenyl)-2-(2,4-difluorophenyl)oxiran-2-yl]methyl}-2,4-dihydro-3H-1,2,4-triazole-3-thione (1638897-70-7)+SX, 2-{[(2S,3R)-3-(2-chlorophenyl)-2-(2,4-difluorophenyl)oxiran-2-yl]methyl}-2,4-dihydro-3H-1,2,4-triazole-3-thione (1638897-71-8)+SX, 2-{[(2R,3R)-3-(2-chlorophenyl)-2-(2,4-difluorophenyl)oxiran-2-yl]methyl}-2,4-dihydro-3H-1,2,4-triazole-3-thione (1638897-72-9)+SX, 2-{[(2S,3S)-3-(2-chlorophenyl)-2-(2,4-difluorophenyl)oxiran-2-yl]methyl}-2,4-dihydro-3H-1,2,4-triazole-3-thione (1638897-73-0)+SX, 1-{[3-(2-chlorophenyl)-2-(2,4-difluorophenyl)oxiran-2-yl]methyl}-1H-1,2,4-triazol-5-yl thiocyanate (1342260-26-7)+SX, 1-{[(2R,3S)-3-(2-chlorophenyl)-2-(2,4-difluorophenyl)oxiran-2-yl]methyl}-1H-1,2,4-triazol-5-yl thiocyanate (1638897-82-1)+SX, 1-{[(2S,3R)-3-(2-chlorophenyl)-2-(2,4-difluorophenyl)oxiran-2-yl]methyl}-1H-1,2,4-triazol-5-yl thiocyanate (1638897-84-3)+SX, 1-{[(2R,3R)-3-(2-chlorophenyl)-2-(2,4-difluorophenyl)oxiran-2-yl]methyl}-1H-1,2,4-triazol-5-yl thiocyanate (1638897-86-5)+SX, 1-{[(2S,3S)-3-(2-chlorophenyl)-2-(2,4-difluorophenyl)oxiran-2-yl]methyl}-1H-1,2,4-triazol-5-yl thiocyanate (1638897-89-8)+SX, 5-(4-chlorobenzyl)-2-chloromethyl-2-methyl-1-(1H-1,2,4-triazol-1-ylmethyl)cyclopentanol (1394057-11-4)+SX, (1R,2S,5S)-5-(4-chlorobenzyl)-2-chloromethyl-2-methyl-1-(1H-1,2,4-triazol-1-ylmethyl)cyclopentanol (1801930-06-2)+SX, (1S,2R,5S)-5-(4-chlorobenzyl)-2-chloromethyl-2-methyl-1-(1H-1,2,4-triazol-1-ylmethyl)cyclopentanol (1801930-07-3)+SX, (1R,2R,5R)-5-(4-chlorobenzyl)-2-chloromethyl-2-methyl-1-(1H-1,2,4-triazol-1-ylmethyl)cyclopentanol (1801919-53-8)+SX, (1S,2S,5S)-5-(4-chlorobenzyl)-2-chloromethyl-2-methyl-1-(1H-1,2,4-triazol-1-ylmethyl)cyclopentanol (1801919-54-9)+SX, (1R,2R,5S)-5-(4-chlorobenzyl)-2-chloromethyl-2-methyl-1-(1H-1,2,4-triazol-1-ylmethyl)cyclopentanol (1801919-55-0)+SX, (1S,2S,5R)-5-(4-chlorobenzyl)-2-chloromethyl-2-methyl-1-(1H-1,2,4-triazol-1-ylmethyl)cyclopentanol (1801919-56-1)+SX, (1R,2S,5R)-5-(4-chlorobenzyl)-2-chloromethyl-2-methyl-1-(1H-1,2,4-triazol-1-ylmethyl)cyclopentanol (1801919-57-2)+SX, (1S,2R,5S)-5-(4-chlorobenzyl)-2-chloromethyl-2-methyl-1-(1H-1,2,4-triazol-1-ylmethyl)cyclopentanol (1801919-58-3)+SX, methyl=3-[(4-chlorophenyl)methyl]-2-hydroxy-1-methyl-2-(1H-1,2,4-triazol-1-ylmethyl)cyclopentanecarboxylate (1791398-02-1)+SX, methyl=(1R,2S,3S)-3-[(4-chlorophenyl)methyl]-2-hydroxy-1-methyl-2-(1H-1,2,4-triazol-1-ylmethyl)cyclopentanecarboxylate (2080743-90-2)+SX, methyl=(1S,2R,3R)-3-[(4-chlorophenyl)methyl]-2-hydroxy-1-methyl-2-(1H-1,2,4-triazol-1-ylmethyl)cyclopentanecarboxylate (2080743-91-3)+SX, methyl=(1R,2R,3R)-3-[(4-chlorophenyl)methyl]-2-hydroxy-1-methyl-2-(1H-1,2,4-triazol-1-ylmethyl)cyclopentanecarboxylate (2080743-92-4)+SX, methyl=(1S,2S,3S)-3-[(4-chlorophenyl)methyl]-2-hydroxy-1-methyl-2-(1H-1,2,4-triazol-1-ylmethyl)cyclopentanecarboxylate (2080743-93-5)+SX, methyl=(1R,2R,3S)-3-[(4-chlorophenyl)methyl]-2-hydroxy-1-methyl-2-(1H-1,2,4-triazol-1-ylmethyl)cyclopentanecarboxylate (2080743-94-6)+SX, methyl=(1S,2S,3R)-3-[(4-chlorophenyl)methyl]-2-hydroxy-1-methyl-2-(1H-1,2,4-triazol-1-ylmethyl)cyclopentanecarboxylate (2080743-95-7)+SX, methyl=(1R,2S,3R)-3-[(4-chlorophenyl)methyl]-2-hydroxy-1-methyl-2-(1H-1,2,4-triazol-1-ylmethyl)cyclopentanecarboxylate (2081061-22-3)+SX, methyl=(1S,2R,3S)-3-[(4-chlorophenyl)methyl]-2-hydroxy-1-methyl-2-(1H-1,2,4-triazol-1-ylmethyl)cyclopentanecarboxylate (2081061-23-4)+SX, 2-chloromethyl-5-(4-fluorobenzyl)-2-methyl-1-(1H-1,2,4-triazol-1-ylmethyl)cyclopentanol (1394057-13-6)+SX, (1R,2S,5S)-2-chloromethyl-5-(4-fluorobenzyl)-2-methyl-1-(1H-1,2,4-triazol-1-ylmethyl)cyclopentanol (1801930-08-4)+SX, (1S,2R,5R)-2-chloromethyl-5-(4-fluorobenzyl)-2-methyl-1-(1H-1,2,4-triazol-1-ylmethyl)cyclopentanol (1801930-09-5)+SX, (1R,2R,5R)-2-chloromethyl-5-(4-fluorobenzyl)-2-methyl-1-(1H-1,2,4-triazol-1-ylmethyl)cyclopentanol (1638898-08-4)+SX, (1S,2S,5S)-2-chloromethyl-5-(4-fluorobenzyl)-2-methyl-1-(1H-1,2,4-triazol-1-ylmethyl)cyclopentanol (1638898-10-8)+SX, (1R,2R,5S)-2-chloromethyl-5-(4-fluorobenzyl)-2-methyl-1-(1H-1,2,4-triazol-1-ylmethyl)cyclopentanol (1638898-13-1)+SX, (1S,2S,5R)-2-chloromethyl-5-(4-fluorobenzyl)-2-methyl-1-(H-1,2,4-triazol-1-ylmethyl)cyclopentanol (1638898-16-4)+SX, (1R,2S,5R)-2-chloromethyl-5-(4-fluorobenzyl)-2-methyl-1-(1H-1,2,4-triazol-1-ylmethyl)cyclopentanol (1638898-20-0)+SX, (1S,2R,5S)-2-chloromethyl-5-(4-fluorobenzyl)-2-methyl-1-(1H-1,2,4-triazol-1-ylmethyl)cyclopentanol (1638898-24-4)+SX, (R)-2-[2-chloro-4-(4-chlorophenoxy)phenyl]-1-(1,2,4-triazol-1-yl)pent-3-yn-2-ol (1801919-59-4)+SX, (R)-2-[4-(4-chlorophenoxy)-2-(trifluoromethyl)phenyl]-1-(1,2,4-triazol-1-yl)propan-2-ol (1616236-94-2)+SX, (R)-1-[4-(4-chlorophenoxy)-2-(trifluoromethyl)phenyl]-1-cyclopropyl-2-(1,2,4-triazol-1-yl)ethanol (1801919-60-7)+SX, (R)-2-[4-(4-chlorophenoxy)-2-(trifluoromethyl)phenyl]-3-methyl-1-(1,2,4-triazol-1-yl)butan-2-ol (1801919-61-8)+SX, 3-[5-(4-chlorophenyl)-2,3-dimethyl-1,2-oxazolidin-3-yl]pyridine (847749-37-5)+SX, *Agrobacterium radiobacter* K1026+SX, *Agrobacterium radiobacter* K84+SX, *Bacillus amyloliquefaciens* AT332+SX, *Bacillus amyloliquefaciens* B3+SX, *Bacillus amyloliquefaciens* D747+SX, *Bacillus amyloliquefaciens* DB101+SX, *Bacillus amyloliquefaciens* DB102+SX, *Bacillus amyloliquefaciens* GB03+SX, *Bacillus amyloliquefaciens* FZB24+SX, *Bacillus amyloliquefaciens* FZB42+SX, *Bacillus amyloliquefaciens* IN937a+SX, *Bacillus amyloliquefaciens* MBI600+SX, *Bacillus amyloliquefaciens* QST713+SX, *Bacillus amyloliquefaciens* isolate B246+SX, *Bacillus amyloliquefaciens* F727+SX, *Bacillus licheniformis* HB-2+SX, *Bacillus licheniformis* SB3086+SX, *Bacillus pumilus* AQ717+SX, *Bacillus pumilus* BUF-33+SX, *Bacillus pumilus* GB34+SX, *Bacillus pumilus* QST2808+SX, *Bacillus simplex* CGF2856+SX, *Bacillus subtilis* AQ153+SX, *Bacillus subtilis* AQ743+SX, *Bacillus subtilis* BU1814+SX, *Bacillus subtilis* D747+SX, *Bacillus subtilis* DB101+SX, *Bacillus subtilis* FZB24+SX, *Bacillus subtilis* GB03+SX, *Bacillus subtilis* HA10404+SX, *Bacillus subtilis* IAB/BS03+SX, *Bacillus subtilis* MBI600+SX, *Bacillus subtilis* QST30002/AQ30002+SX, *Bacillus subtilis* QST30004/AQ30004+SX, *Bacillus subtilis* QST713+SX, *Bacillus subtilis* QST714+SX, *Bacillus subtilis* var. *Amyloliquefaciens* FZB24+SX, *Bacillus subtilis* Y1336+SX, *Burkholderia cepacia*+SX, *Burkholderia cepacia* type Wisconsin J82+SX, *Burkholderia cepacia* type Wisconsin M54+SX, *Candida oleophila* O+SX, *Candida saitoana*+SX, *Chaetomium* cupreum+SX, *Clonostachys rosea*+SX, *Coniothyrium minitans* CGMCC8325+SX, *Coniothyrium minitans* CON/M/91-8+SX, *Cryptococcus albidus*+SX, *Erwinia carotovora* subsp. *carotovora* CGE234M403+SX, *Fusarium oxysporum* Fo47+SX, *Gliocladium catenulatum* J1446+SX, *Paenibacillus polymyxa* AC-1+SX, *Paenibacillus polymyxa* BS-0105+SX, *Pantoea agglomerans* E325+SX, *Phlebiopsis gigantea* VRA1992+SX, *Pseudomonas aureofaciens* TX-1+SX, *Pseudomonas chlororaphis* 63-28+SX, *Pseudomonas chlororaphis* MA342+SX, *Pseudomonas fluorescens* 1629RS+SX, *Pseudomonas fluorescens* A506+SX, *Pseudomonas fluorescens* CL145A+SX, *Pseudomonas fluorescens* G7090+SX, *Pseudomonas* sp. CAB-02+SX, *Pseudomonas syringae* 742RS+SX, *Pseudomonas syringae* MA-4+SX, *Pseudozyma flocculosa* PF-A22UL+SX, *Pseudomonas rhodesiae* HAI-0804+SX, *Pythium oligandrum* DV74+SX, *Streptomyces griseoviridis* K61+SX, *Streptomyces lydicus* WYCD108US+SX, *Streptomyces lydicus* WYEC108+SX, *Talaromyces flavus* SAY-Y-94-01+SX, *Talaromyces flavus* V117b+SX, *Trichoderma asperellum* ICC012+SX, *Trichoderma asperellum* SKT-1+SX, *Trichoderma asperellum* T34+SX, *Trichoderma atroviride* CNCM 1-1237+SX, *Trichoderma atroviride* LC52+SX, *Trichoderma atroviride* SC1+SX, *Trichoderma atroviride* SKT-1+SX, *Trichoderma gamsii* ICC080+SX, *Trichoderma harzianum* 21+SX, *Trichoderma harzianum* DB104+SX, *Trichoderma harzianum* DSM 14944+SX, *Trichoderma harzianum* ESALQ-1303+SX, *Trichoderma harzianum* ESALQ-1306+SX, *Trichoderma harzianum* IIHR-Th-2+SX, *Trichoderma harzianum* kd+SX, *Trichoderma harzianum* MO1+SX, *Trichoderma harzianum* SF+SX, *Trichoderma harzianum* T22+SX, *Trichoderma harzianum* T39+SX, *Trichoderma harzianum* TH35+SX, *Trichoderma polysporum* I1M206039+SX, *Trichoderma stromaticum*+SX, *Trichoderma virens* G-41+SX, *Trichoderma virens* GL-21+SX, *Trichoderma viride*+SX, *Variovorax paradoxus* CGF4526+SX, Harpin protein+SX, *Trichoderma harzianum* ITEM908+SX, *Trichoderma harzianum* T78+SX, methyl ({2-methyl-5-[1-(4-methoxy-2-methylphenyl)-1H-pyrazol-3-yl]phenyl}methyl)carbamate (1605879-98-8)+SX, 2-(difluoromethyl)-N-[1,1,3-trimethyl-2,3-dihydro-1H-inden-4-yl]pyridine-3-carboxamide (1616239-21-4)+SX, 2-(difluoromethyl)-N-[3-ethyl-1,1-dimethyl-2,3-dihydro-1H-inden-4-yl]pyridine-3-carboxamide (1847460-02-9)+SX, 2-(difluoromethyl)-N-[3-propyl-1,1-dimethyl-2,3-dihydro-1H-inden-4-yl]pyridine-3-carboxamide (1847460-05-2)+SX, (2E,3Z)-5-{[1-(4-chlorophenyl)-1H-pyrazol-3-yl]oxy}-2-(methoxyimino)-N,3-dimethylpent-3-enamide (1445331-27-0)+SX, *Bacillus amyloliquefaciens* subsp. *plantarum* D747+SX, *Pythium oligandrum* M1+SX, *Tricho-* derma asperellum T25+SX, Trichoderma asperellum TV1+SX, Trichoderma atroviride IMI 206040+SX, Trichoderma atroviride T11+SX, Bacillus amyloliquefaciens (Aveo (trademark) EZ Nematicide)+SX.

Combinations of the Present ingredient in the above Group (c) and the Present compound:

1-methylcyclopropene+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyclanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, Gibberellin A+SX, Gibberellin A3+SX, inabenfide+SX, Kinetin+SX, maleic hydrazide+SX, mefluidide+SX, mepiquat-chloride+SX, oxidized glutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tribufos+SX, trinexapac-ethyl+SX, uniconazole-P+SX, 2-(naphthalen-1-yl)acetamide+SX, [4-oxo-4-(2-phenylethyl)amino]butyric acid+SX, methyl 5-(trifluoromethyl)benzo[b]thiophene-2-carboxylate+SX, 3-[(6-chloro-4-phenylquinazolin-2-yl)amino]-1-propanol+SX, formononetin+SX, *Glomus intraradices*+SX, *Glomus mosseae*+SX, *Glomus aggregatum*+SX, *Glomus etunicatum*+SX, *Bradyrhizobium elkani*+SX, *Bradyrhizobium japonicum*+SX, *Bradyrhizobium lupini*+SX, *Rhizobium leguminosarum* bv. *trifolii*+SX, *Rhizobium leguminosarum* bv. *phaseoli*+SX, *Rhizobium leguminosarum* bv. *viciae*+SX, *Sinorhizobium meliloti*+SX, *Rhizobium fredii*+SX, *Rhizobium loti*+SX, *Rhizobium trifolii*+SX, *Rhizobium tropici*+SX, 1,3-diphenylurea+SX, *Azorhizobium caulinodans*+SX, *Azospirillum amazonense*+SX, *Azospirillum brasilense* XOH+SX, *Azospirillum brasilense* Ab-V5+SX, *Azospirillum brasilense* Ab-V6+SX, *Azospirillum caulinodans*+SX, *Azospirillum halopraeferens*+SX, *Azospirillum irakense*+SX, *Azospirillum lipoferum*+SX, *Bradyrhizobium elkanii* SEMIA 587+SX, *Bradyrhizobium elkanii* SEMIA 5019+SX, *Bradyrhizobium japonicum* TA-11+SX, *Bradyrhizobium japonicum* USDA 110+SX, *Bradyrhizobium liaoningense*+SX, *Delftia acidovorans* RAY209+SX, *Gigaspora margarita*+SX, *Gigaspora rosea*+SX, *Glomus deserticola*+SX, *Glomus monosporum*+SX, *Mesorhizobium ciceri*+SX, *Mesorhizobium huakii*+SX, *Rhizophagus clarus*+SX, *Rhizobium etli*+SX, *Rhizobium galegae*+SX, *Rhizophagus irregularis* DAOM 197198+SX, *Paraglomus brasillianum*+SX, *Claroideoglomus claroideum*+SX, lipochitooligosaccharide SP104+SX, Zucchini Yellow Mosaik Virus weak strain+SX.

Combinations of the Present ingredient in the above Group (d) and the Present compound:

allidochlor+SX, benoxacor+SX, cloquintocet+SX, cloquintocet-mexyl+SX, cyometrinil+SX, cyprosulfamide+SX, dichlormid+SX, dicyclonone+SX, dimepiperate+SX, disulfoton+SX, dymron+SX, fenchlorazole+SX, fenchlorazole-ethyl+SX, fenclorim+SX, flurazole+SX, furilazole+SX, fluxofenim+SX, Hexim+SX, isoxadifen+SX, isoxadifen-ethyl+SX, mecoprop+SX, mefenpyr+SX, mefenpyr-ethyl+SX, mefenpyr-diethyl+SX, mephenate+SX, metcamifen+SX, oxabetrinil+SX, 1,8-naphthalic anhydride+SX, 1,8-octamethylene diamine+SX, AD-67 (4-(dichloroacetyl)-1-oxa-4-azaspiro[4.5]decane)+SX, CL-304415 (4-carboxy-3,4-dihydro-2H-1-benzopyran-4-acetic acid)+SX, CSB (1-bromo-4-[(chloromethyl)sulfonyl]benzene)+SX, DKA-24 (2,2-dichloro-N-[2-oxo-2-(2-propenylamino)ethyl]-N-(2-propenyl)acetamide)+SX, MG191 (2-(dichloromethyl)-2-methyl-1,3-dioxolane)+SX, MG-838 (2-propenyl 1-oxa-4-azaspiro[4.5]decane-4-carbodithioate)+SX, PPG-1292 (2,2-dichloro-N-(1,3-dioxan-2-ylmethyl)-N-(2-propenyl)acetamide)+SX, R-28725 (3-(dichloroacetyl)-2,2-dimethyl-1,3-oxazolidine)+SX, R-29148 (3-(dichloroacetyl)-2,2,5-trimethyl-1,3-oxazolidine)+SX, TI-35 (1-(dichloroacetyl)azepane)+SX.

Combinations of the Present ingredient in the above Group (e) and the Present compound:

1-dodecyl-1H-imidazole+SX, N-(2-ethylhexyl)-8,9,10-trinorborn-5-ene-2,3-dicarboximide+SX, bucarpolate+SX, N,N-dibutyl-4-chlorobenzenesulfonamide+SX, dietholate+SX, diethylmaleate+SX, piperonyl butoxide+SX, piperonyl cyclonene+SX, piprotal+SX, propyl isome+SX, safroxan+SX, sesamex+SX, sesamolin+SX, sulfoxide+SX, Verbutin+SX, DMC (1,1-bis(4-chlorophenyl)ethanol)+SX, FDMC (1,1-bis(4-chlorophenyl)-2,2,2-trifluoroethanol)+SX, ETN (1,2-epoxy-1,2,3,4-tetrahydronaphthalene)+SX, ETP (1,1,1-trichloro-2,3-expoxypropane)+SX, PSCP (phenylsaligenin cyclic phosphate)+SX, TBPT (S,S,S-tributyl phosphorotrithioate)+SX, TPP (triphenyl phosphate)+SX.

Combinations of the Present ingredient in the above Group (f) and the Present compound:

anthraquinone+SX, chloralose+SX, acrep+SX, butopyronoxyl+SX, camphor+SX, d-camphor+SX, carboxide+SX, dibutyl phthalate+SX, deet+SX, dimethylcarbate+SX, dimethylphthalate+SX, dibutyl succinate+SX, dibutyl adipate+SX, ethohexadiol+SX, hexamide+SX, icaridin+SX, methoquin-butyl+SX, methylneodecanamide+SX, 2-(octylthio)ethanol+SX, butoxypolypropylene glycol+SX, oxamate+SX, quwenzhi+SX, quyingding+SX, zengxiaon+SX, rebemide+SX, copper naphthenate+SX, zinc naphthenate+SX.

Combinations of the Present ingredient in the above Group (g) and the Present compound:

bis(tributyltin) oxide+SX, allicin+SX, bromoacetamide+SX, cloethocarb+SX, copper sulfate+SX, fentin+SX, ferric phosphate+SX, metaldehyde+SX, niclosamide+SX, pentachlorophenol+SX, sodium pentachlorophenoxide+SX, tazimcarb+SX, tralopyril+SX, trifenmorph+SX.

Combinations of the Present ingredient in the above Group (h) and the Present compound:

(E)-2-hexenal+SX, (E)-2-octadecenal+SX, (E)-4-tridecen-1-yl acetate+SX, (E)-5-decen-1-yl acetate+SX, (E)-5-decen-1-ol+SX, (E)-3,3-dimethylcyclohexylideneacetaldehyde+SX, (E)-7-dodecen-1-yl acetate+SX, (E)-8-dodecen-1-yl acetate+SX, (E)-9-dodecen-1-yl acetate+SX, (E)-10-hexadecenal+SX, (E)-11-hexadecen-1-yl acetate+SX, (E)-11-tetradecen-1-yl acetate+SX, (E)-11-tetradecen-1-ol+SX, (E)-4-tridecen-1-yl acetate+SX, (E)-6-methylhept-2-en-4-ol+SX, (Z)-2-(3,3-dimethylcyclohexylidene)ethanol+SX, (Z)-4-decen-1-yl acetate+SX, (Z)-4-tridecen-1-yl acetate+SX, (Z)-5-decen-1-yl acetate+SX, (Z)-5-decen-1-ol+SX, (Z)-7-tetradecenal+SX, (Z)-7-dodecen-1-yl acetate+SX, (Z)-8-dodecen-1-yl acetate+SX, (Z)-9-dodecen-1-yl acetate+SX, (Z)-8-dodecen-1-ol+SX, (Z)-9-hexadecenal+SX, (Z)-10-hexadecen-1-yl acetate+SX, (Z)-11-hexadecen-1-ol+SX, (Z)-11-hexadecenal+SX, (Z)-11-hexadecen-1-yl acetate+SX, (Z)-11-octadecenal+SX, (Z)-13-octadecenal+SX, (Z)-hexadec-13-en-11-yn-1-yl acetate+SX, (Z)-13-octadecenal+SX, (Z)-icos-13-en-10-one+SX, (Z)-7-tetradecenal+SX, (Z)-tetradec-9-en-1-ol+SX, (Z)-9-tetradecen-1-yl acetate+SX, (Z)-11-tetradecen-1-yl acetate+SX, (Z)-13-icosen-10-one+SX, (Z,E)-7,11-hexadecadien-1-yl acetate+SX, (Z,E)-9,12-tetradecadien-1-yl acetate+SX, (E,Z)-4,10-tetradecadien-1-yl acetate+SX, (E,E)-8,10-dodecadien-1-ol+SX, (E,E)-10,12-hexadecadienal+SX, (E,E)-9,11-tetradecadien-1-yl acetate+SX, (E,Z)-2,13-octadecadien-1-ol+SX, (E,Z)-3,13-octadecadien-1-ol+SX, (E,Z)-2,13-octadecadien-1-yl acetate+SX, (E,Z)-3,13-octadecadien-1-yl acetate+SX, (E,Z)-7,9-dodecadien-1-yl acetate+SX, (E,E)-7,9-dodecadien-1-yl acetate+SX, (Z,E)-9,12-tetradecadien-1-yl acetate+SX, (Z,E)-9,11-tetradecadien-1-yl acetate+SX, (Z,E)-7,11-hexadecadien-1-yl acetate+SX, (Z,Z)-3,13-octadecadien-1-ol+SX, (Z,Z)-4,7-decadien-1-yl acetate+SX, (Z,Z)-3,13-octadecadien-1-yl acetate+SX, (Z,Z)-7,11-hexadecadien-1-yl acetate+SX, (Z,Z,E)-7,11,13-hexadecatrienal+SX, (5R)-5-[(1Z)-1-decen-1-yl]dihydro-2(3H)-furanone+SX, (2R,5R)-ethyl-1,6-dioxaspiro[4,4]nonane+SX, (2R,5S)-ethyl-1,6-dioxaspiro[4,4]nonane+SX, (4R,8R)-4,8-dimethyldecanal+SX, (4R,8S)-4,8-dimethyldecanal+SX, 2,4-dimethyl-5-ethyl-6,8-dioxabicyclo[3,2,1]octane+SX, (−)-4-methyl-3-heptanol+SX, 1,7-dioxaspiro[5,5]undecane+SX, 3-carene+SX, 3-methylcyclohex-2-en-1-one+SX, 14-methyloctadec-1-ene+SX, 4-methylnonan-5-ol+SX, 4-methylnonan-5-one+SX, 4-(3-oxobutyl)phenyl acetate+SX, dodecyl acetate+SX, dodeca-8,10-dien-1-yl acetate+SX, ethyl (2E,4Z)-decadienoate+SX, ethyl 4-methyloctanoate+SX, methyl 2,6,10-trimethyldodecanoate+SX, tetradecan-1-ol+SX, tetradec-11-en-1-ol+SX, tetradec-11-en-1-yl acetate+SX, tridec-4-en-1-yl acetate+SX, (3S,6R)-3-methyl-6-isopropenyl-9-decen-1-yl acetate+SX, (3S,6S)-3-methyl-6-isopropenyl-9-decen-1-yl acetate+SX, alpha-multistriatin+SX, alpha-pinene+SX, endo-brevicomin+SX, exo-brevicomin+SX, camphene+SX, codlelure+SX, codlemone+SX, cuelure+SX, disparlure+SX, dominicalure+SX, eugenol+SX, farnesol+SX, ferrolure+SX, frontalin+SX, gossyplure+SX, grandlure+SX, grandlure I+SX, grandlure II+SX, grandlure III+SX, grandlure IV+SX, hexalure+SX, ipsdienol+SX, ipsenol+SX, japonilure+SX, lineatin+SX, litlue+SX, looplure+SX, medlure+SX, megatomoic acid+SX, methyleugenol+SX, muscalure+SX, nerolidol+SX, orfralure+SX, oryctalure+SX, ostramone+SX, rhyncolure+SX, siglure+SX, sordidin+SX, sulcatol+SX, trimedlure+SX, trimedlure A+SX, trimedlure B1+SX, trimedlure B2+SX, trimedlure C+SX, trunc-call+SX, (E)-verbenol+SX, (Z)-verbenol+SX, trans-verbenol+SX, (S)-verbenone+SX.

Examples of the mixture ratio of the Present compound and the Present ingredient include, but are not limited to, 1000:1 to 1:1000, 500:1 to 1:500, 100:1 to 1:100, 50:1 to 1:50, 20:1 to 1:20, 10:1 to 1:10, 3:1 to 1:3, 1:1 to 1:500, 1:1 to 1:100, 1:1 to 1:50, 1:1 to 1:20, and 1:1 to 1:10 in the ratio by weight (Present compound:Present ingredient).

The Present compounds have control effects on harmful arthropods such as harmful insects and harmful mites, harmful nematodes, harmful mollusks, and animal endoparasite (Protozoa and worm such as nematode, rematode, cestode, and acanthocephala). Examples of the harmful arthropods, harmful nematodes, harmful mollusks, and animal endoparasites include, but are not limited to, the followings.

Hemiptera:

from the family Delphacidae, for example, small brown planthopper (*Laodelphax striatellus*), brown planthopper (*Nilaparvata lugens*), white-backed planthopper (*Sogatella furcifera*), corn planthopper (*Peregrinus maidis*), cereal leafhopper (*Javesella pellucida*), sugarcane leafhopper (*Perkinsiella saccharicida*), and *Tagosodes orizicolus*; from the family Cicadellidae, for example, green rice leafhopper (*Nephotettix cincticeps*), green paddy leafhopper (*Nephotettix virescens*), rice leafhopper (*Nephotettix nigropictus*), zigzag-striped leafhopper (*Recilia dorsalis*), tea green leafhopper (*Empoasca onukii*), potato leafhopper (*Empoasca fabae*), corn leafhopper (*Dalbulus maidis*), and rice leafhopper (*Cofana spectra*);

from the family Cercopidae, for example, *Mahanarva posticata* and *Mahanarva fimbriolata*;

from the family Aphididae, for example, bean aphid (*Aphis fabae*), soybean aphid (*Aphis glycines*), cotton aphid (*Aphis gossypii*), green apple aphid (*Aphis pomi*), apple aphid (*Aphis spiraecola*), green peach aphid (*Myzus persicae*), leaf-curling plum aphid (*Brachycaudus helichrysi*), cabbage aphid (*Brevicoryne brassicae*), rosy apple aphid (*Dysaphis plantaginea*), false cabbage aphid (*Lipaphis erysimi*), potato aphid (*Macrosiphum euphorbiae*), foxglove aphid (*Aulacorthum solani*), lettuce aphid (*Nasonovia ribisnigri*), grain aphid (*Rhopalosiphum padi*), corn aphid (*Rhopalosiphum maidis*), brown citrus aphid (*Toxoptera citricida*), mealy plum aphid (*Hyalopterus pruni*), cane aphid (*Melanaphis sacchari*), black rice root aphid (*Tetraneura nigriabdominalis*), sugarcane cottony aphid (*Ceratovacuna lanigera*), and apple woolly aphid (*Eriosoma lanigerum*);

from the family Phylloxeridae, for example, grapevine phylloxera (*Daktulosphaira vitifoliae*), Pecan phylloxera (*Phylloxera devastatrix*), Pecan leaf phylloxera (*Phylloxera notabilis*), and Southern pecan leaf phylloxera (*Phylloxera russellae*);

from the family Adelgidae, for example, hemlock woolly aphid (*Adelges tsugae*), *Adelges piceae*, and *Aphrastasia pectinatae*;

from the family Pentatomidae, for example, black rice bug (*Scotinophara lurida*), Malayan rice black bug (*Scotinophara coarctata*), common green stink bug (*Nezara antennata*), white-spotted spined bug (*Eysarcoris aeneus*), lewis spined bug (*Eysarcoris lewisi*), white-spotted bug (*Eysarcoris ventralis*), *Eysarcoris annamita*, brown marmorated stink bug (*Halyomorpha halys*), green plant bug (*Nezara viridula*), Brown stink bug (*Euschistus heros*), Red banded stink bug (*Piezodorus guildinii*), *Oebalus pugnax*, and *Dichelops melacanthus*;

from the family Cydnidae, for example, Burrower brown bug (*Scaptocoris castanea*);

from the family Alydidae, for example, bean bug (*Riptortus pedestris*), corbett rice bug (*Leptocorisa chinensis*), and rice bug (*Leptocorisa acuta*);

from the family Coreidae, for example, Cletus punctiger and Australian leaf-footed bug (*Leptoglossus australis*); from the family Lygaeidae, for example, oriental chinch bug (*Caverelius saccharivorus*), seed bug (*Togo hemipterus*), and chinch bug (*Blissus leucopterus*);

from the family Miridae, for example, rice leaf bug (*Trigonotylus caelestialium*), sorghum plant bug (*Stenotus rubrovittatus*), wheat leaf bug (*Stenodema calcarata*), and American tarnished plant bug (*Lygus lineolaris*);

from the family Aleyrodidae, for example, greenhouse whitefly (*Trialeurodes vaporariorum*), tobacco whitefly (*Bemisia tabaci*), citrus whitefly (*Dialeurodes citri*), citrus spiny whitefly (*Aleurocanthus spiniferus*), tea spiny whitefly (*Aleurocanthus camelliae*), and Pealius euryae;

from the family Diaspididae, for example, *Abgrallaspis cyanophylli*, red scale (*Aonidiella aurantii*), San José scale (*Diaspidiotus perniciosus*), white peach scale (*Pseudaulac-* aspis pentagona), arrowhead scale (*Unaspis yanonensis*), and citrus snow scale (*Unaspis citri*);

from the family Coccidae, for example, pink wax scale (*Ceroplastes rubens*);

from the family Margarodidae, for example, fluted scale (*Icerya purchasi*) and seychelles fluted scale (*Icerya seychellarum*);

from the family Pseudococcidae, for example, *solanum* mealybug (*Phenacoccus solani*), cotton mealybug (*Phenacoccus solenopsis*), Japanese mealybug (*Planococcus kraunhiae*), white peach scale (*Pseudococcus comstocki*), citrus mealybug (*Planococcus citri*), currant mealybug (*Pseudococcus calceolariae*), long-tailed mealybug (*Pseudococcus longispinus*), and tuttle mealybug (*Brevennia rehi*);

from the family Psyllidae, for example, citrus *psylla* (*Diaphorina citri*), two-spotted citrus psyllid (*Trioza erytreae*), pear sucker (*Cacopsylla* pyrisuga), *Cacopsylla chinensis*, potato psyllid (*Bactericera cockerelli*), and Pear psylla (*Cacopsylla pyricola*);

from the family Tingidae, for example, sycamore lace bug (*Corythucha ciliata*), aster tingid (*Corythucha marmorata*), Japanese pear lace bug (*Stephanitis nashi*), and azalea lace bug (*Stephanitis pyrioides*);

from the family Cimicidae, for example, common bed bug (*Cimex lectularius*) and tropical bed bug (*Cimex hemipterus*);

from the family Cicadidae, for example, Giant Cicada (*Quesada gigas*);

Triatoma spp. (such as *Triatoma infestans*);
Reduvius spp. (such as *Reduvius senilis*);
Arilus spp. (such as *Arilus critatus*);
Rhodnius spp. (such as *Rhodnius prolixus*);
Triatoma spp. (such as *Triatoma rubrofasciata*);
Panstrongylus ssp.;
and the others.

Lepidoptera:

from the family Crambidae, for example, rice stem borer (*Chilo suppressalis*), Dark-headed stem borer (*Chilo polychrysus*), white stem borer (*Scirpophaga innotata*), yellow paddy borer (*Scirpophaga incertulas*), *Rupela albina*, rice leaf roller (*Cnaphalocrocis medinalis*), *Marasmia patnalis*, rice leaf roller (*Marasmia exigua*), cotton leaf roller (*Notarcha derogata*), corn borer (*Ostrinia furnacalis*), European corn borer (*Ostrinia nubilalis*), cabbage webworm (*Hellula undalis*), grape leafroller (*Herpetogramma* luctuosale), bluegrass webworm (*Pediasia teterrellus*), rice case-worm (*Nymphula depunctalis*), and Sugarcane borer (*Diatraea saccharalis*);

from the family Pyralidae, for example, lesser cornstalk borer (*Elasmopalpus lignosellus*), mealworm moth (*Plodia interpunctella*), and persimmon bark borer (*Euzophera batangensis*);

from the family Noctuidae, for example, cotton worm (*Spodoptera litura*), beet armyworm (*Spodoptera exigua*), rice armyworm (*Mythimna separata*), cabbage moth (*Mamestra brassicae*), pink borer (*Sesamia inferens*), grass armyworm (*Spodoptera mauritia*), green rice caterpillar (*Naranga aenescens*), *Spodoptera frugiperda*, true armyworm (*Spodoptera exempta*), black cutworm (*Agrotis ipsilon*), beet worm (*Autographa nigrisigna*), rice looper (*Plusia festucae*), soybean looper (*Chrysodeixis includens*), *Trichoplusia* spp., *Heliothis* spp. (such as tobacco budworm (*Heliothis virescens*)), *Helicoverpa* spp. (such as tobacco budworm (*Helicoverpa armigera*) and corn earworm (*Helicoverpa zea*)), Velvetbean caterpillar (*Anticarsia gemmatalis*), Cotton leafworm (*Alabama argillacea*), and Hop vine borer (*Hydraecia immanis*);

from the family Pieridae, for example, common cabbage worm (*Pieris rapae*);

from the family Tortricidae, for example, oriental fruit moth (*Grapholita molesta*), *Grapholita dimorpha*, soybean moth (Leguminivora glycinivorella), *Matsumuraeses azukivora*, summer fruit *tortrix* (*Adoxophyes orana fasciata*), smaller tea *tortrix* (*Adoxophyes honmai*), Japanese tea *tortrix* (*Hoinona magnanima*), apple *tortrix* (*Archips fuscocupreanus*), codling moth (*Cydia pomonella*), sugarcane shoot borer (*Tetramoera schistaceana*), Bean Shoot Borer (*Epinotia aporema*), and Citrus fruit borer (*Ecdytolopha aurantiana*);

from the family Gracillariidae, for example, tea leaf roller (*Caloptilia theivora*) and Asiatic apple leaf miner (*Phyllonorycter ringoniella*);

from the family Carposinidae, for example, peach fruit moth (*Carposina sasakii*);

from the family Lyonetiidae, for example, Coffee Leaf miner (*Leucoptera coffeella*), peach leaf miner (*Lyonetia clerkella*), and *Lyonetia prunifoliella;* from the family Lymantriidae, for example, *Lymantria* spp. (such as gypsy moth (*Lymantria dispar*)) and *Euproctis* spp. (such as tea lymantriid (*Euproctis pseudoconspersa*));

from the family Plutellidae, for example, diamondback moth (*Plutella xylostella*);

from the family Gelechiidae, for example, peach worm (*Anarsia lineatella*), sweetpotato leaf folder (*Helcystogramma triannulella*), pink bollworm (*Pectinophora gossypiella*), potato moth (*Phthorimaea operculella*), and *Tuta absoluta;* from the family Arctiidae, for example, American white moth (*Hyphantria cunea*);

from the family Castniidae, for example, Giant Sugarcane borer (*Telchin licus*);

from the family Cossidae, for example, *Cossus insularis;* from the family Geometridae, for example, *Ascotis selenaria;* from the family Limacodidae, for example, blue-striped nettle grub (*Parasa lepida*);

from the family Stathmopodidae, for example, persimmon fruit moth (*Stathmopoda masinissa*);

from the family Sphingidae, for example, tobacco hornworm (*Acherontia lachesis*);

from the family Sesiidae, for example, Nokona feralis, cherry borer (*Synanthedon hector*), and *Synanthedon tenuis;* from the family Hesperiidae, for example, rice skipper (*Parnara guttata*);

from the family Tineidae, for example, casemaking clothes moth (*Tinea translucens*) and common clothes moth (*Tineola bisselliella*);

and the others.

Thysanoptera:

from the family Thripidae, for example, western flower *thrips* (*Frankliniella occidentalis*), oriental *thrips* (*Thrips palmi*), yellow tea *thrips* (*Scirtothrips dorsalis*), onion *thrips* (*Thrips tabaci*), eastern flower *thrips* (*Frankliniella intonsa*), rice *thrips* (*Stenchaetothrips biformis*), and *Echinothrips americanus*;

from the family Phlaeothripidae, for example, aculeated rice *thrips* (*Haplothrips aculeatus*);

and the others.

Diptera:

from the family Anthomyiidae, for example, seedcorn maggot (*Delia platura*), onion maggot (*Delia antiqua*), and beet leaf miner (*Pegomya cunicularia*);

from the family Ulidiidae, for example, sugarbeet root maggot (*Tetanops myopaeformis*);

from the family Agromyzidae, for example, rice leaf miner (*Agromyza oryzae*), tomato leaf miner (*Liriomyza sativae*), chrysanthemum leaf miner (*Liriomyza trifolii*), and pea leafminer (*Chromatomyia horticola*);

from the family Chloropidae, for example, rice stem maggot (*Chlorops oryzae*);

from the family Tephritidae, for example, melon fly (*Bactrocera cucurbitae*), oriental fruit fly (*Bactrocera dorsalis*), Malaysian fruit fly (*Bactrocera latifrons*), olive fruit fly (*Bactrocera oleae*), Queensland fruit fly (*Bactrocera tryoni*), Mediterranean fruit fly (*Ceratitis capitata*), apple maggot (*Rhagoletis pomonella*), and Japanese cherry fruit fly (Rhacochlaena *japonica*);

from the family Ephydridae, for example, smaller rice leaf miner (*Hydrellia griseola*), whorl maggot (*Hydrellia philippina*), and paddy stem maggot (*Hydrellia sasakii*);

from the family Drosophilidae, for example, cherry drosophila (*Drosophila suzukii*);

from the family Phoridae, for example, *Megaselia spiracularis;* from the family Psychodidae, for example, *Clogmia albipunctata;* from the family Sciaridae, for example, *Bradysia difformis;* from the family Cecidomyiidae, for example, hessian fly (*Mayetiola destructor*) and paddy gall fly (*Orseolia oryzae*);

from the family Diopsidae, for example, *Diopsis macrophthalma;* from the family Tipulidae, for example, rice crane fly (*Tipula aino*), Common cranefly (*Tipula oleracea*), and European cranefly (*Tipula paludosa*);

from the family Culicidae, for example, southern house mosquito (*Culex pipiens pallens*), dengue mosquito (*Aedes aegypti*), Asian tiger mosquito (*Aedes albopictus*), Chinese malaria mosquito (*Anopheles hyracanus sinensis*), *Culex quinquefasciatus, Culex pipiens molestus* Forskal, brown house mosquito (*Culex quinquefasciatus*), *Anopheles gambiae, Anopheles mininus, Anopheles stephensi,* and *Anopheles albimanus;* from the family Simulidae, for example, *Prosimulium yezoensis* and *Simulium ornatum;* from the family Tabanidae, for example, *Tabanus trigonus;* from the family Muscidae, for example, house fly (*Musca domestica*), false stable fly (*Muscina stabulans*), biting house fly (*Stomoxys calcitrans*), and buffalo fly (*Haematobia irritans*);

from the family Calliphoridae;

from the family Sarcophagidae;

from the family Chironomidae, for example, *Chironomus plumosus, Chironomus yoshimatsui,* and *Glyptotendipes tokunagai;* from the family Fannidae;

and the others.

Coleoptera:

from the family Chrysomelidae, for example, western corn rootworm (*Diabrotica virgifera virgifera*), southern corn rootworm (*Diabrotica undecimpunctata howardi*), northern corn rootworm (*Diabrotica barberi*), Mexican corn rootworm (*Diabrotica virgifera zeae*), banded cucumber beetle (*Diabrotica balteata*), Cucurbit Beetle (*Diabrotica speciosa*), bean leaf beetle (*Cerotoma trifurcata*), barley leaf beetle (*Oulema melanopus*), cucurbit leaf beetle (*Aulacophora femoralis*), striped flea beetle (*Phyllotreta striolata*), Cabbage flea beetle (*Phyllotreta cruciferae*), Western black flea beetle (*Phyllotreta pusilla*), Cabbage stem flea beetle (*Psylliodes chrysocephala*), Colorado potato beetle (*Leptinotarsa decemlineata*), rice leaf beetle (*Oulema oryzae*), grape *colaspis* (*Colaspis brunnea*), corn flea beetle (*Chaetocnema pulicaria*), sweet-potato flea beetle (*Chaetocnema confinis*), potato flea beetle (*Epitrix cucumeris*), rice leaf beetle (*Dicladispa armigera*), southern corn leaf beetle (*Myochrous denticollis*), *Laccoptera quadrimaculata,* and tobacco flea beetle (*Epitrix hirtipennis*);

from the family Carabidae, for example, Seedcorn beetle (*Stenolophus lecontei*) and slender seed-corn ground beetle (*Clivina impressifrons*);

from the family Scarabaeidae, for example, cupreus chafer (*Anomala cuprea*), soybean beetle (*Anomala rufocuprea*), *Anomala albopilosa,* Japanese beetle (*Popillia japonica*), yellowish elongate chafer (*Heptophylla picea*), European Chafer (*Rhizotrogus majalis*), *Tomarus gibbosus, Holotrichia* spp., *Phyllophaga* spp. (such as June beetle (*Phyllophaga crinita*)), and *Diloboderus* spp. (such as *Diloboderus abderus*);

from the family Curculionidae, for example, coffee bean weevil (*Araecerus coffeae*), sweet-potato weevil (*Cylas formicarius*), West Indian sweet-potato weevil (*Euscepes postfasciatus*), alfalfa weevil (*Hypera postica*), maize wevil (*Sitophilus zeamais*), rice plant weevil (*Echinocnemus squameus*), rice water weevil (*Lissorhoptrus oryzophilus*), *Rhabdoscelus lineatocollis,* boll weevil (*Anthonomus grandis*), nunting billbug (*Sphenophorus venatus*), Southern Corn Billbug (*Sphenophorus callosus*), Soybean stalk weevil (*Sternechus subsignatus*), Sugarcane weevil (*Sphenophorus levis*), rusty gourd-shaped weevil (*Scepticus griseus*), brown gourd-shaped weevil (*Scepticus uniformis*), Mexican bean weevil (*Zabrotes subfasciatus*), pine beetle (*Tomicus piniperda*), Coffee Berry Borer (*Hypothenemus hampei*), *Aracanthus* spp. (such as *Aracanthus mourei*), and cotton root borer (*Eutinobothrus brasiliensis*);

from the family Tenebrionidae, for example, red meal beetle (*Tribolium castaneum*) and mason beetle (*Tribolium confusum*);

from the family Coccinellidae, for example, twenty-eight-spotted ladybird (*Epilachna vigintioctopunctata*);

from the family Bostrychidae, for example, common powder-post beetle (*Lyctus brunneus*);

from the family Ptinidae;

from the family Cerambycidae, for example, citrus long-horned beetle (*Anoplophora malasiaca*) and *Migdolus fryanus;* from the family Elateridae, for example, *Melanotus okinawensis,* barley wireworm (*Agriotes fuscicollis*), *Melanotus legatus, Anchastus* spp., *Conoderus* spp., *Ctenicera* spp., *Limonius* spp., and *Aeolus* spp.;

from the family Staphylinidae, for example, *Paederus fuscipes;* from the family Dermestidae, for example, varied carpet beetle (*Anthrenus verbasci*) and hide beetle (*Dermestes maculates*);

from the family Anobiidae, for example, tobacco beetle (*Lasioderma serricorne*) and biscuit beetle (*Stegobium paniceum*);

and the others.

Orthoptera:

from the family Acrididae, for example, oriental migratory locust (*Locusta migratoria*), Moroccan locust (*Do-

*ciostaurus maroccanus*), Australian plague locust (*Chortoicetes terminifera*), red locust (*Nomadacris septemfasciata*), Brown Locust (*Locustana pardalina*), Tree Locust (*Anacridium melanorhodon*), Italian Locust (*Calliptamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearwinged grasshopper (*Camnula pellucida*), desert locust (*Schistocerca gregaria*), Yellow-winged locust (*Gastrimargus musicus*), Spur-throated locust (*Austracris guttulosa*), Japanese grasshopper (*Oxya yezoensis*), rice grasshopper (*Oxya japonica*), and Bombay locust (*Patanga succincta*);

from the family Gryllotalpidae, for example, oriental mole cricket (*Gryllotalpa orientalis*);

from the family Gryllidae, for example, house cricket (*Acheta domestica*) and emma field cricket (*Teleogryllus emma*);

from the family Tettigoniidae, for example, Mormon cricket (*Anabrus simplex*);

and the others.

Hymenoptera:

from the family Tenthredinidae, for example, beet sawfly (*Athalia rosae*) and nippon cabbage sawfly (*Athalia japonica*);

from the family Formicidae, for example, *Solenopsis* spp. (such as red imported fire ant (*Solenopsis invicta*) and tropical fire ant (*Solenopsis geminata*)), *Atta* spp. (such as Brown leaf-cutting ant (*Atta capiguara*)), *Acromyrmex* spp., *Paraponera clavata*, black house ant (*Ochetellus glaber*), little red ant (*Monomorium pharaonis*), Argentine ant (*Linepi thema humile*), *Formica fusca japonica*, *Pristomyrmex punctutus*, *Pheidole noda*, big-headed ant (*Pheidole megacephala*), *Camponotus* spp. (such as *Camponotus japonicus* and *Camponotus obscuripes*), *Pogonomyrmex* spp. (such as western harvester ant (*Pogonomyrmex occidentalis*)), *Wasmania* spp. (such as *Wasmania auropunctata*), and long-legged ant (*Anoplolepis gracilipes*);

from the family Vespidae, for example, Asian giant hornet (*Vespa mandarinia japonica*), *Vespa simillima*, *Vespa analis Fabriciusi*, Asian hornet (*Vespa velutina*), and *Polistes jokahamae*;

from the family Siricidae, for example, pine wood wasp (*Urocerus gigas*);

from the family Bethylidae;

and the others.

Blattodea:

from the family Blattellidae, for example, German cockroach (*Blattella germanica*);

from the family Blattidae, for example, smoky-brown cockroach (*Periplaneta fuliginosa*), American cockroach (*Periplaneta americana*), brown cockroach (*Periplaneta brunnea*), and black cockroach (*Blatta orientalis*);

from the family Termitidae, for example, Japanese termite (*Reticulitermes speratus*), Formosan termite (*Coptotermes formosanus*), western drywood termite (*Incisitermes minor*), *Cryptotermes domesticus*, *Odontotermes formosanus*, *Neotermes koshunensis*, *Glyptotermes satsumensis*, *Glyptotermes nakajimai*, *Glyptotermes fuscus*, *Hodotermopsis sjostedti*, *Coptotermes guangzhouensis*, *Reticulitermes amamianus*, *Reticulitermes miyatakei*, *Reticulitermes kanmonensis*, *Nasutitermes takasagoensis*, *Pericapritermes nitobei*, *Sinocapritermes mushae*, and *Cornitermes cumulans*;

and the others.

Siphonaptera:

cat flea (*Ctenocephalides felis*), dog flea (*Ctenocephalides canis*), human flea (*Pulex irritans*), oriental rat flea (*Xenopsylla cheopis*), chigoe flea (*Tunga penetrans*), chicken flea (*Echidnophaga gallinacea*), and European rat flea (*Nosopsyllus fasciatus*);

and the others.

Anoplura:

pig louse (*Haematopinus suis*), short-nosed cattle louse (*Haematopinus eurysternus*), *Dalmalinia ovis*, *Linognathus seypsus*, *Pediculus humanis*, *Pediculuc humanus corporis*, *Pediculus humanus humanus*, and *Phthirus pubis*;

and the others.

Mallophagida:

*Bovicola* spp. (such as *Dalmalinia bovis* and *Dalmalinia ovis*), *Trichodectes* spp. (such as *Trichodectes canis*), *Felocpla* spp. (such as *Felicola subrostrata*), and *Lipeurus* spp. (such as *Lipeurus caponis*);

from the family Menoponidae, for example, *Trimenopon* spp. and *Menopon* spp.;

and the others.

Acari:

from the family Tetranychidae, for example, common red spider mite (*Tetranychus urticae*), kanzawa spider mite (*Tetranychus kanzawai*), red spider mite (*Tetranychus evansi*), citrus red mite (*Panonychus citri*), fruit-tree red spider mite (*Panonychus ulmi*), and *Oligonychus* spp.;

from the family Eriophyidae, for example, Japanese citrus rust mite (*Aculops pelekassi*), *Phyllocoptruta citri*, tomato mite (*Aculops lycopersici*), purple mite (*Calacarus carinatus*), tea rust mite (*Acaphylla theavagrans*), *Eriophyes chibaensis*, apple bud mite (*Aculus schlechtendali*), *Aceria diospyri*, *Aceria tosichella*, and *Shevtchenkella* sp.;

from the family Tarsonemidae, for example, broad mite (*Polyphagotarsonemus latus*);

from the family Tenuipalpidae, for example, *Brevipalpus phoenicis*;

from the family Tuckerellidae;

from the family Ixodidae, for example, *Haemaphysalis longicornis*, *Haemaphysalis flava*, *Haemaphysalis campanulata*, *Dermacentor taiwanensis*, American dog tick (*Dermacentor variabilis*), *Dermacentor andersoni*, *Ixodes holocyclus*, *Ixodes ovatus*, *Ixodes persulcatus*, *Ixodes pacificus*, *Ixodes ricinus*, black-legged tick (*Ixodes scapularis*), lone star tick (*Amblyomma americanum*), gulf coast tick (*Amblyomma maculatum*), *Boophilus microplus*, *Boophilus annulatus*, *Rhipicephalus appendiculatus*, and brown dog tick (*Rhipicephalus sanguineus*);

from the family Acaridae, for example, cereal mite (*Tyrophagus putrescentiae*) and grassland mite (*Tyrophagus similis*);

from the family Pyroglyphidae, for example, American house dust mite (*Dermatophagoides farinae*) and European house dust mite (*Dermatophagoides pteronyssinus*);

from the family Cheyletidae, for example, *Cheyletus eruditus*, *Cheyletus malaccensis*, *Cheyletus moorei*, *Cheyletiella yasguri*, and *Cheyletiella blakei*;

from the family Sarcoptidae, for example, *Notoedres cati*, *Notoedres muris*, *Ornithodorus hermsi*, *Ornithodorus turicata*, mange mite (*Otodectes cynotis*), sheep scab mite (*Psoroptes ovis*), horse psoroptic mange mite (*Psoroptes equi*), and itch mite (*Sarcoptes scabiei*);

from the family Demodicidae, for example, dog follicle mite (*Demodex canis*) and cat follicle mite (*Demodex cati*);

from the family Listrophoridae;

from the family Haplochthoniidae;

from the family Macronyssidae, for example, tropical rat mite (*Ornithonyssus bacoti*) and feather mite (*Ornithonyssus sylviarum*);

from the family Dermanyssidae, for example, bird mite (*Dermanyssus gallinae*);

from the family Trombiculidae, for example, *Leptotrombidium akamushi*, *Trombicula pallida*, and *Trombicula scutellaris*;

*Argas* spp. (such as fowl tick (*Argas persicus*));
*Knemidocoptes* spp. (such as *Knemidocoptes mutans*);
*Listrophorus* spp. (such as *Listrophorus gibbus*);
*Chorioptes* spp.;
*Hypodectes* spp.;
*Pterolichus* spp.;
*Cytodites* spp.;
*Laminosioptes* spp.;
*Varroa* spp. (such as *Varroa jacobsoni*);
*Ornithocheyletia* spp.;
*Myobia* spp.;
*Psorergates* spp.;
and the others.

Araneae:
from the family Eutichuridae, for example, *Cheiracanthium japonicum*;
from the family Theridiidae, for example, red-back spider (*Latrodectus hasseltii*);
and the others.

Polydesmida:
from the family Paradoxosomatidae, for example, flat-backed millipede (*Oxidus gracilis*) and *Nedyopus tambanus*;
and the others.

Isopoda:
from the family Armadillidiidae, for example, common pill bug (*Armadillidium vulgare*);
and the others.

Chilopoda:
from the family Scutigeridae, for example, *Thereuonema hilgendorfi*;
from the family Scolopendridae, for example, giant tropical centipede (*Scolopendra subspinipes*);
from the family Ethopolyidae, for example, *Bothropolys rugosus*;
and the others.

Gastropoda:
from the family Limacidae, for example, tree slug (*Limax marginatus*) and garden tawny slug (*Limax flavus*);
from the family Philomycidae, for example, *Meghimatium bilineatum*;
from the family Ampullariidae, for example, golden apple snail (*Pomacea canaliculata*);
from the family Lymnaeidae, for example, *Austropeplea ollula*;
and the others.

Nematoda:
from the family Aphelenchoididae, for example, rice white-tip nematode (*Aphelenchoides besseyi*);
from the family Pratylenchidae, for example, root lesion nematode (*Pratylenchus coffeae*), *Pratylenchus* brachyurus, California meadow nematode (*Pratylenchus neglectus*), and *Radopholus similis*;
from the family Heteroderidae, for example, javanese root-knot nematode (*Meloidogyne javanica*), southern root-knot nematode (*Meloidogyne incognita*), northern root-knot nematode (*Meloidogyne hapla*), soybean cyst nematode (*Heterodera glycines*), potato cyst nematode (*Globodera rostochiensis*), and white potato cyst nematode (*Globodera pallida*);

from the family Hoplolaimidae, for example, *Rotylenchulus reniformis*;

from the family Anguinidae, for example, strawberry bud nematode (*Nothotylenchus acris*) and stem nematode (*Ditylenchus dipsaci*);

from the family Tylenchulidae, for example, citrus nematode (*Tylenchulus semipenetrans*);

from the family Longidoridae, for example, dagger nematode (*Xiphinema index*);

from the family Trichodoridae;

from the family Parasitaphelenchidae, for example, pine wilt disease (*Bursaphelenchus xylophilus*);

and the others.

Protozoa:
for example, *Trypanosoma* spp., *Leishmania* spp., *Trichomonas* spp., *Monocercomonas* spp., *Hexamita* spp., *Histomonas* spp., *Giardia* spp., *Entamoeba* spp., *Naegleria* spp., *Acanthamoeba* spp., *Balantidium* spp., *Eimeria* spp., *Isospora* spp., *Hammondia* spp., *Toxoplasma* spp., *Sarcocystis* spp., *Besnoitia* spp., *Cryptosporidium* spp., *Hepatozoon* spp., *Leucocytozoon* spp., *Plasmodium* spp., *Hepatocyctis* spp., *Babesia* spp., *Theileria* spp., *Cytauxzoon* spp., *Neospora* spp., *Pneumocyctis* spp., and *Encephalistozoon* spp.

Enoplida:
for example, *Trichuris* spp., *Capillaria* spp., *Trichomosoides* spp., and *Trichinella* spp.;

Rhabditia:
for example, *Micronema* spp. and *Strongyloides* spp.;

Strongylida:
for example, *Stronylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Parelaphostrongylus* spp., *Angiostrongylus* spp., *Aelurosutrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., and *Ollulanus* spp.

Oxyurida:
for example, *Oxyuris* spp., *Enterobius* spp., *Passalurus* spp., *Syphacia* spp., *Aspiculuris* spp., and *Heterakis* spp.

Ascaridia:
for example, *Ascaris* spp., *Toxascaris* spp., *Toxocara* spp., *Parascaris* spp., *Anisakis* spp., and *Ascaridia* spp.

Spirurida:
for example, *Gnathostoma* spp., *Physaloptera* spp., *Thelazia* spp., *Gongylonema* spp., *Habronema* spp., *Parabronema* spp., *Draschia* spp., and *Dracunculus* spp.

Filariida:
for example, *Stephanofilaria* spp., *Parafilaria* spp., *Setaria* spp., *Loa* spp., *Dirofilaria* spp., *Litomosoides* spp., *Brugia* spp., *Wuchereria* spp., and *Onchocerca* spp.

Gigentorhynchida:
for example, *Filicollis* spp., *Moniliforumis* spp., *Macracanthorhynchus* spp., and *Prosthenorchis* spp.

The target harmful arthropods such as harmful insects and harmful mites, harmful mollusks, harmful nematodes, and internal parasites of animals may have a reduced agent-sensitivity to or a developed agent-resistance to an insecticide, a miticide, a molluscicide, a nematicide, and an antiparasitic drug. However, when the agent-sensitivity is greatly reduced or the agent-resistance is greatly developed, a composition of the present invention comprising an insecticide, a miticide, a molluscicide, a nematicide, and an antiparasitic drug other than the intended insecticide, miticide, molluscicide, nematicide, and antiparasitic drug is preferably used.

The Present compounds may be also used to protect plants from plant diseases caused by insect-borne viruses or insect-borne bacteria.

Examples of the insect-borne viruses are recited as follows.

Rice tungro spherical virus, Rice tungro bacilliform virus, Rice grassy stunt virus, Rice ragged stunt virus, Rice stripe virus, Rice black streaked dwarf virus, Southern rice black-streaked dwarf virus, Rice gall dwarf virus, Rice hoja blanca virus, Rice yellow stunt virus, Rice yellow mottle virus, Rice dwarf virus, Northern cereal mosaic virus, Barley yellow dwarf virus, Barley mild mosaic virus, Barley yellow dwarf virus-PAV, Cereal yellow dwarf virus-RPS, Wheat yellow leaf virus, Oat sterile dwarf virus, Wheat streak mosaic virus, Maize dwarf mosaic virus, Maize stripe virus, Maize chlorotic mottle virus, Maize chlorotic dwarf virus, Maize rayado fino virus, Sugarcane mosaic virus, Fiji disease virus, Sugarcane yellow leaf virus, Soybean mild mosaic virus, Cycas necrotic stunt virus, Soybean dwarf virus, Milk vetch dwarf virus, Soybean mosaic virus, Alfalfa mosaic virus, Bean yellow mosaic virus, Bean common mosaic virus, Southern bean mosaic virus, Peanut stunt virus, Broad bean wilt virus 1, Broad bean wilt virus 2, Broad bean necrosis virus, Broad bean yellow vein virus, Clover yellow vein virus, Peanut mottle virus, Tobacco streak virus, Bean pod mottle virus, Cowpea chlorotic mottle virus, Mung bean yellow mosaic virus, Soybean crinkle leaf virus, Tomato chlorosis virus, Tomato spotted wilt virus, Tomato yellow leaf curl virus, Tomato aspermy virus, Tomato infectious chlorosis virus, Potato leafroll virus, Potato virus Y, Melon yellow spot virus, Melon necrotic spot virus, Watermelon mosaic virus, Cucumber mosaic virus, Zucchini yellow mosaic virus, Turnip mosaic virus, Turnip yellow mosaic virus, Cauliflower mosaic virus, Lettuce mosaic virus, Celery mosaic virus, Beet mosaic virus, Cucurbit chlorotic yellows virus, Capsicum chlorosis virus, Beet pseudo yellows virus, Leak yellow stripe virus, Onion yellow dwarf virus, Sweet potato feathery mottle virus, Sweet potato shukuyo mosaic virus, Strawberry mottle virus, Strawberry mild yellow edge virus, Strawberry pseudo mild yellow edge virus, Strawberry crinkle virus, Strawberry vein banding virus, plum pox virus, Chrysanthemum stem necrosis virus, Impatiens necrotic spot virus, Iris yellow spot virus, Lily mottle virus, Lilly symptomless virus, Tulip mosaic virus, and the others.

Examples of the insect-borne bacteria are recited as follows.

*Candidatus Phytoplasma oryzae, Candidatus Phytoplasma asteris, Maize bushy stunt phytoplasma, Candidatus Liberbacter asiaticus, Candidatus Liberbacter africanus, Candidatus Liberbacter americanus*, and the others.

The Present compounds may also be used for protecting animals from animal diseases caused by insect-borne viruses. Examples of the animal diseases caused by the insect-borne viruses on which the Present compounds have control effects include the followings.

Enzootic encephalitis, Vesicular stomatitis, Rift Valley fever, bluetongue, Akabane disease, Chuzan disease, Lumpy skin disease, Bovine leukosis, Aino virus infection, Ibaraki disease, Bovine ephemeral fever, Nairobi sheep disease, Sheep pox, Goat pox, Equine infectious anemia, African horse sickness, Fowl pox, and Myxomatosis.

The Present compounds may also be used for protecting animals from animal diseases caused by insect-borne bacteria, rickettsias, spirochetes, or fungi. Examples of the animal diseases caused by the insect-borne bacteria, rickettsias, spirochetes, or fungi on which the Present compounds have control effects include the followings.

Tularemia, Anaplasmosis, Rickettsiosis, Ehrlichiosis, Lyme disease, and Pseudofarcy in horses.

The composition for controlling harmful arthropods of the present invention comprises the Present compound or the Composition X and inert carrier(s) (hereinafter referred to as "Present composition"). The Present composition is usually prepared by mixing the Present compound or the Composition X with inert carrier(s) such as solid carrier(s), liquid carrier(s), and gaseous carrier(s), and as needed, adding surfactant(s) and other auxiliary agent(s) for formulation, to formulate into an emulsifiable concentrate, an oil solution, a dust formulation, a granule, a wettable powder, a granular wettable powder, a flowable, a dry flowable, a microcapsule, an aerosol, a poison bait, a resin formulation, a shampoo formulation, a paste-like formulation, a foam, a carbon dioxide formulation, a tablet, a chewable tablet, a microsphere formulation, an implant formulation, or the like. Such formulation may be processed into and used as a mosquito repellent coil, an electric mosquito repellent mat, a liquid mosquito repellent formulation, a smoking agent, a fumigant, a sheet formulation, a spot-on formulation, or a formulation for oral treatment. The Present composition usually comprises 0.0001 to 95% by weight of the Present compound or the Composition X.

Examples of the solid carrier(s) to be used in the formulation include fine powders and granules of clays (for example, kaolin clay, diatomaceous earth, bentonite, Fubasami clay, and acid white clay), dry silica, wet silica, talc, ceramic, other inorganic minerals (for example, sericite, quartz, sulfur, active carbon, and calcium carbonate), chemical fertilizers (for example, ammonium sulfate, ammonium phosphate, ammonium nitrate, urea, and ammonium chloride), and the others; as well as synthetic resins (for example, polyester resins such as polypropylene, polyacrylonitrile, polymethylmethacrylate, and polyethylene terephthalate; nylon resins such as nylon-6, nylon-11, and nylon-66; polyamide resins; polyvinyl chloride, polyvinylidene chloride, vinyl chloride-propylene copolymers, and the others).

Examples of the liquid carrier(s) include water; alcohols (for example, methanol, ethanol, isopropyl alcohol, butanol, hexanol, benzyl alcohol, ethylene glycol, propylene glycol, and phenoxy ethanol); ketones (for example, acetone, methyl ethyl ketone, and cyclohexanone); aromatic hydrocarbons (for example, toluene, xylene, ethyl benzene, dodecyl benzene, phenyl xylyl ethane, and methylnaphthalene); aliphatic hydrocarbons (for example, hexane, cyclohexane, kerosene, and light oil); esters (for example, ethyl acetate, butyl acetate, isopropyl myristate, ethyl oleate, diisopropyl adipate, diisobutyl adipate, and propylene glycol monomethyl ether acetate); nitriles; ethers (for example, diisopropyl ether, 1,4-dioxane, 1,2-dimethoxyethane, diethylene glycol dimethyl ether, diethylene glycol monomethyl ether, propylene glycol monomethyl ether, dipropylene glycol monomethyl ether, and 3-methoxy-3-methyl-1-butanol); amides (for example, dimethylformamide (hereinafter referred to as "DMF") and N,N-dimethylacetamide); sulfoxides (for example, dimethyl sulfoxide); propylene carbonate; and vegetable oils (for example, sesame oil, corn oil, olive oil, and cottonseed oil).

Examples of the gaseous carrier(s) include fluorocarbon, butane gas, LPG (liquefied petroleum gas), dimethyl ether, and carbon dioxide.

Examples of the surfactant(s) include nonionic surfactants such as polyoxyethylene alkyl ethers, polyoxyethylene alkyl aryl ethers, and polyethylene glycol fatty acid esters; and anionic surfactants such as alkyl sulfonates and alkylbenzene sulfonates, and alkyl sulfates.

Examples of the other auxiliary agent(s) for formulation include binders, dispersants, colorants, and stabilizers. Specific examples thereof include casein, gelatin, saccharides (for example, starch, gum arabic, cellulose derivatives, and alginic acid), lignin derivatives, bentonite, water-soluble synthetic polymers (for example, polyvinyl alcohol, polyvinyl pyrrolidone, and polyacrylic acids), acidic isopropyl phosphate, 2,6-di-tert-butyl-4-methylphenol, and BRA (a mixture of 2-tert-butyl-4-methoxyphenol and 3-tert-butyl-4-methoxyphenol).

Examples of the base material of the resin formulation include vinyl chloride polymers, polyurethane, and the others, and plasticizer(s) such as phthalic acid esters (for example, dimethyl phthalate and dioctyl phthalate), adipic acid esters, and stearic acid may also be added to these base materials, as needed. The resin formulation may be prepared by mixing a compound with the above-mentioned base material, kneading the mixture in a conventional kneading apparatus, followed by molding it by injection molding, extrusion molding, pressure molding, or the like. The resultant resin formulation may be subjected to further molding, cutting procedure, or the like, as needed, to be processed into a shape such as plate, film, tape, net, and string shapes. These resin formulations may be processed into an animal collar, an animal ear tag, a sheet formulation, a trap string, a gardening support, or other products.

Examples of the base material for the poison bait include grain powders, vegetable oils, saccharides, crystalline celluloses, and the others, and further, antioxidant(s) such as dibutylhydroxytoluene and nordihydroguaiaretic acid, preservative(s) such as dehydroacetic acid, accidental ingestion inhibitor(s) for children and pets such as chili powder, insect attraction fragrance(s) such as cheese flavor, onion flavor, and peanut oil, or the other ingredient(s) may be added thereto as needed.

The method for controlling harmful arthropods of the present invention is carried out by applying an effective amount of the Present compound or the Composition X to harmful arthropods directly and/or habitats where harmful arthropods live (for example, plant bodies, soil, interiors of houses, and animal bodies). Also, the Present compound may be applied to seeds. In the method for controlling harmful arthropods of the present invention, the Present compound or the Composition X is usually used in the form of the Present composition. Examples of the method for applying the Present compound or the Composition X include foliage treatment, soil treatment, root treatment, shower treatment, smoking treatment, water surface treatment, and seed treatment.

In the present invention, examples of the plants include whole plants, foliages, flowers, ears, fruits, tree stems, branches, tree crowns, seeds, vegetative reproduction organs, and seedlings.

A vegetative reproduction organ means a part of plant such as root, stem, and leaf which has a growth capability even when said part is separated from the plant body and placed into soil. Examples of the vegetative reproduction organ include tuberous root, creeping root, bulb, corm or solid bulb, tuber, rhizome, stolon, rhizophore, cane cuttings, propagule, and vine cutting. Stolon is also referred to as "runner", and propagule is also referred to as "propagulum" and categorized into broad bud and bulbil. Vine cutting means a shoot (collective term of leaf and stem) of sweet potato, glutinous yam, or the like. Bulb, corm or solid bulb, tuber, rhizome, cane cuttings, rhizophore, and tuberous root are also collectively referred to as "bulb". For example, cultivation of potato starts with planting a tuber into soil, and the tuber to be used is generally referred to as "seed potato".

Examples of the method for applying an effective amount of the Present compound or the Composition X to plants or soil for cultivating plants include a method for applying an effective amount of the Present compound or the Composition X to plants, a method for applying an effective amount of the Present compound or the Composition X to seeds or vegetative reproduction organs such as seed disinfection, seed soaking, and seed coating, and a method for applying an effective amount of the Present compound or the Composition X to soil before or after planting plants.

When the Present composition is used for controlling harmful arthropods in the agricultural field, the application dose as an amount of the Present compound is usually within the range from 1 to 10,000 g per 10,000 $m^2$. When the Present composition is applied to seeds or vegetative reproduction organs, the application dose as an amount of the Present compound is usually within the range from 0.001 to 100 g per 1 Kg of the seeds or vegetative reproduction organs. The application dose of the Composition X is usually within the range from 0.001 to 100 g per 1 kg of the seeds or vegetative reproduction organs. An emulsifiable concentrate, a wettable powder, a flowable, or the like of Present composition is usually applied by diluting it with water in such a way that a concentration of the active ingredient is within the range from 0.01 to 10,000 ppm. A granule, a dust formulation, or the like is usually applied as itself without diluting it.

These formulations and diluents of the formulations with water may be directly sprayed to harmful arthropods or plants such as crops to be protected from harmful arthropods, or applied to soil in cultivated areas to control harmful arthropods that inhabit the soil.

Also, a resin formulation processed into a sheet shape or a string shape may be wrapped around crops, stretched near crops, spread on plant foot soil, or the like.

When the Present composition is used to control harmful arthropods that live inside a house, the application dose as an amount of the Present compound is usually within the range from 0.01 to 1,000 mg per 1 $m^2$ of an area to be treated in the case of using it on a planar area. In the case of using it spatially, the application dose as an amount of the Present compound is usually within the range from 0.01 to 500 mg per 1 $m^3$ of the space to be treated. When the Present composition is formulated into an emulsifiable concentrate, a wettable powder, a flowable, or the like, such formulation is usually applied after diluting it with water in such a way that a concentration of the active ingredient is within the range from 0.1 to 10,000 ppm, and then sparging it. In the case of being formulated into an oil solution, an aerosol, a smoking agent, a poison bait, or the like, such formulation is used as itself without diluting it.

Examples of the animals to which the Present compounds are administered include homothermal animals and poikilothermic animals which are fed as livestock or pets. Examples of the homothermal animals include mammals such as cows, water buffalos, sheep, goats, pigs, camels, deers, fallow deers, reindeers, horses, donkeys, dogs, cats, rabbits, ferrets, mice, rats, hamsters, squirrels, and monkeys; fur animals such as minks, chinchillas, and raccoons; and birds such as chickens, geese, turkeys, ducks, pigeons, parrots, and quails. Examples of the poikilothermic animals include reptiles such as tortoises, sea turtles, red-eared turtles, spotted turtles, lizards, iguanas, chameleons, geckos, pythons, colubrids, and cobras; and fish such as freshwater fish (for example, trouts, carp, and eels) and salt-water fish. Among the above animals, cows, horses, pigs, sheep, goats, chickens, dogs, and cats are especially preferable.

When the Present composition is used for controlling external parasites of livestock such as cows, horses, pigs, sheep, goats, and chickens; and small animals such as dogs, cats, rats, and mice, the Present composition may be applied to the animals by a known method in the veterinary field. Examples of the specific method for using the Present composition include a method for orally or parenterally administering the Present composition to host animals such as livestock and small animals.

(1) Oral Administration Methods

When the Present composition is administered to an animal as an oral formulation, it may be used in the form of, for example, a liquid (for example, an emulsifiable concentrate, an oil solution, an oily liquid, an aqueous liquid, a solution, or a suspension), a gel, a dust formulation, a granule, a paste-like formulation, a tablet, a chewable tablet, a soft chewable tablet, a bolus, a capsule, a premix for animal feed, a syrup, or the like.

(2) Parenteral Administration Methods (a) External Administration Methods for Skin When the Present composition is administered to an animal as an external agent for skin, it may be used in the form of, for example, a liquid (for example, an emulsifiable concentrate, an oil solution, an oily liquid, an aqueous liquid, a solution, or a suspension), a dust formulation, a cream, an ointment, an aerosol formulation, a sheet formulation, or the like, and may be administered by spot-on treatment, pour-on treatment, soaking, spraying, applying, bathing, washing, rubbing in, dusting, or the like. Spot-on treatment is usually a method wherein a liquid is added dropwise or applied to a skin of host animal from the head to the tail. Pour-on treatment is usually a method wherein a liquid is poured into a host animal along the mid-dorsal line.

(b) Administration Methods by Injection

When the Present composition is administered to an animal as an injectable formulation, it may be administered by intraruminal injection, intramuscular injection, intravenous injection, intraperitoneal injection, drip infusion, sustained release injection, or subcutaneous injection.

(c) Other Administration Methods

The Present composition may be administered to an animal as a suppository, an implant formulation (for example, an implant tablet, a formulation which is formed by using a biodegradable polymer as a base material, or a formulation which is encapsulated by a biocompatible metal such as titanium and releases an active ingredient at a constant rate), or a resin formulation having an appropriate shape such as collar and ear tag.

The dose of the Present compound to an animal may vary depending on the target animal or external parasites to be controlled, and is usually 0.1 to 5,000 mg/kg per 1 kg of live weight of the target animal. In the case of oral administration methods and administration methods by injection, the dose is preferably within the range from 1 to 100 mg/kg. In the case of external administration methods for skin, the dose is preferably within the range from 1 to 1,000 mg/kg.

In the dosage form of formulation used in the above veterinary administration methods, various organic or inorganic carrier materials conventionally used as formulation materials are used, and added to solid formulations as excipients, lubricants, binders, or disintegrants; and added to liquid formulations as solvents, solubilizing agents, suspending agents, tonicity agents, buffers, soothing agents, or the like. Also, formulation additives such as preservatives, antioxidants, colorants, and sweetening agents may be used, as needed. Preferable examples of the excipients include lactose, white soft sugar, D-mannitol, D-sorbitol, starch, pregelatinized starch, dextrin, crystalline cellulose, low substituted hydroxypropylcellulose, carboxymethylcellulose sodium, gum arabic, dextrin, pullulan, light anhydrous silicic acid, synthetic aluminum silicate, and magnesium aluminometasilicate. Preferable examples of the lubricants include magnesium stearate, calcium stearate, talc, and colloidal silica. Preferable examples of the binders include pregelatinized starch, sucrose, gelatin, gum arabic, methylcellulose, carboxymethylcellulose, carboxymethylcellulose sodium, crystalline cellulose, white soft sugar, D-mannitol, trehalose, dextrin, pullulan, hydroxypropylcellulose, hydroxypropyl methylcellulose, and polyvinylpyrrolidone. Preferable examples of the disintegrants include lactose, white soft sugar, starch, carboxymethylcellulose, carboxymethylcellulose calcium, croscarmellose sodium, sodium carboxymethyl starch, light anhydrous silicic acid, and low substituted hydroxypropylcellulose. Preferable examples of the solvents include water (for example, ion exchanged water, pure water, ultrapure water, purified water, and water for injection), physiological saline, Ringer's solution, alcohols, ketones, aromatic hydrocarbons, aliphatic hydrocarbons, vegetable oils, esters, nitriles, ethers, amides, halogenated hydrocarbons, pyrrolidones (for example, N-methylpyrrolidone and N-octylpyrrolidone), and propylene carbonate. Preferable examples of the solubilizing agents include polyethylene glycol, propylene glycol, D-mannitol, trehalose, benzyl benzoate, ethanol, tris-aminomethane, cholesterol, triethanolamine, sodium carbonate, sodium citrate, sodium salicylate, and sodium acetate. Preferable examples of the suspending agents include surfactants such as stearyltriethanolamine, sodium lauryl sulfate, laurylaminopropionic acid, lecithin, benzalkonium chloride, benzethonium chloride, and glycerin monostearate; hydrophilic polymers such as polyvinyl alcohol, polyvinylpyrrolidone, carboxymethylcellulose sodium, methylcellulose, hydroxymethylcellulose, hydroxyethylcellulose, and hydroxypropylcellulose; polysorbates, polyoxyethylene hydrogenated castor oil, alkyl sulfuric acid esters, alkyl acetic acid esters, alkyl sulfonates, alkyl aryl sulfonates, alkyl aryl ethers and polyoxyethylene adducts thereof, polyoxyethylene glycol ethers, polyhydric alcohol esters, and sugar alcohol derivatives. Preferable examples of the tonicity agents include sodium chloride, glycerin, D-mannitol, D-sorbitol, and glucose. Preferable examples of the buffers include buffer solutions such as phosphates, acetates, carbonates, and citrates. Preferable examples of the soothing agents include benzyl alcohol. Preferable examples of the preservatives include paraoxybenzoic acid esters, chlorobutanol, benzyl alcohol, phenethyl alcohol, dehydroacetic acid, and sorbic acid. Preferable examples of the antioxidants include sulfites and ascorbates. Preferable examples of the colorants include water-soluble food tar dyes (for example, food dyes such as food red No. 2 and No. 3, food yellow No. 4 and No. 5, and food blue No. 1 and No. 2; water-insoluble lake dyes (for example, aluminum salts of water-soluble food tar dyes), and natural dyes (for example, @-carotene, chlorophyll, and red iron oxide). Preferable examples of the sweetening agents include sugar, glucose, fructose, sucrose, xylitol, and artificial sweeteners (for example, aspartame and saccharin).

Also, an injection may be prepared by dissolving an active ingredient into, suspending an active ingredient in, or emulsifying an active ingredient in an aqueous solvent (for example, distilled water, physiological saline, or Ringer's solution), an oil solvent (for example, a vegetable oil or propylene glycol), or the like with dispersant(s) (for example, polysorbate 80, polyoxyethylene hydrogenated castor oil 60, polyethylene glycol, carboxymethylcellulose, or sodium alginate), preservative(s) (for example, methylparaben, propylparaben, benzyl alcohol, chlorobutanol, or phenol), tonicity agent(s), or the like. In this case, additive(s) such as stabilizer(s) (for example, human serum albumin), solubilizing agent(s), and soothing agent(s) may be optionally used. An injection solution is usually filled into an appropriate ampule.

The Present composition may also be used as a sustained-release formulation. Examples of the sustained-release formulation include a microcapsule (for example, microsphere•microcapsule or microparticle) prepared by a drying in water method (for example, o/w method or w/o/w method), a phase separation method, a spray dry method, or a similar method thereof, and a formulation formed by a biocompatible polymer (for example, polylactic acid or lactic acid•glycolic acid copolymer), collagen, gelatin, or silicone.

Also, the Present composition may be used as an agent for controlling harmful arthropods in croplands such as fields, paddy fields, grasses, and orchards. The Present composition can control harmful arthropods in croplands and the others in which the following plants and the others are cultivated.

corn, rice, wheat, barley, rye, oat, sorghum, cotton, soybean, peanut, buckwheat, beet, rapeseed, sunflower, sugar cane, tobacco, solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, welsh onion, onion, garlic, and asparagus), ammiaceous vegetables (for example, carrot, parsley, celery, and parsnip), chenopodiaceous vegetables (for example, spinach and Swiss chard), lamiaceous vegetables (for example, perilla, mint, and basil), strawberry, sweet potato, glutinous yam, eddoe, flowers, foliage plants, pomaceous fruits (for example, apple, pear, Japanese pear, Chinese quince, and quince), stone fleshy fruits (for example, peach, plum, nectarine, Japanese apricot (*Prunus mume*), cherry fruit, apricot, and prune), citrus fruits (for example, Citrus unshiu, orange, lemon, lime, and grapefruit), nuts (for example, chestnuts, walnuts, hazelnuts, almond, pistachio, cashew nuts, and macadamia nuts), berry fruits (for example, blueberry, cranberry, blackberry, and raspberry), grapes, Japanese persimmon, olive, Japanese plum, banana, coffee, date palm, coconuts, tea, mulberry, flowering plants, roadside trees (for example, ash, birch, dogwood, eucalyptus, ginkgo (*Ginkgo biloba*), lilac, maple, oak (*quercus*), poplar, Judas tree, Formosan gum (*Liquidambar formosana*), plane tree, zelkova, Japanese arborvitae (*Thuja standishii*), fir wood, hemlock, juniper, pinus, picea, and yew (*Taxus cuspidate*)), turfs, grasses, and the others.

The above plants may be genetically modified plants.

EXAMPLES

The following Examples including Preparation Examples, Formulation Examples, and Test Examples serve to illustrate the present invention more in detail, but the present invention is not limited to these Examples only.

First, Preparation Examples of the Present compounds are shown below.

Reference Preparation Example 1-1

A mixture of 2-[6-chloro-3-(ethanesulfonyl)pyridin-2-yl]-3-methyl-6-(trifluoromethyl)-3H-imidazo[4,5-b]pyridine (40.5 g), a 28% aqueous solution of ammonia (87.6 mL), and N-methylpyrrolidone (200 mL) was stirred at 100° C. for 2 hours. To the resulting mixture was added water, and the precipitated solids were collected by filtration. The resulting solids were washed sequentially with water and MTBE to give the Intermediate compound (1) represented by the following formula (30.1 g).

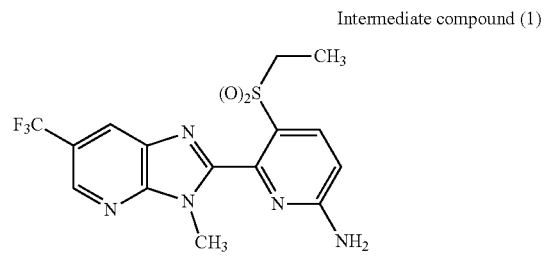

Intermediate compound (1)

$^1$H-NMR (CDCl$_3$) δ: 8.73 (1H, dd, J=2.0, 0.7 Hz), 8.28 (1H, dd, J=2.0, 0.5 Hz), 8.15 (1H, d, J=8.8 Hz), 6.73 (1H, d, J=8.8 Hz), 5.15 (2H, s), 3.85 (3H, s), 3.59 (2H, q, J=7.5 Hz), 1.32 (3H, t, J=7.5 Hz).

Reference Preparation Example 1-2

The compound prepared according to the method described in the Reference Preparation Example 1-1 and the physical property thereof are shown below.

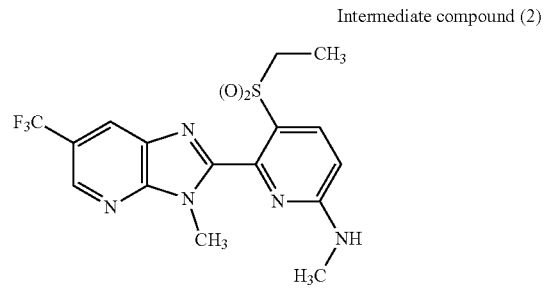

Intermediate compound (2)

$^1$H-NMR (CDCl$_3$) δ: 8.73 (1H, s), 8.29 (1H, s), 8.11 (1H, d, J=8.8 Hz), 6.61 (1H, d, J=8.8 Hz), 5.27 (1H, s), 3.86 (3H, s), 3.61 (2H, q, J=7.5 Hz), 3.04 (3H, d, J=5.2 Hz), 1.32 (3H, t, J=7.5 Hz).

Reference Preparation Example 2-1

A mixture of the Intermediate compound (1) (4.0 g), N-bromosuccinimide (2.03 g), and chloroform (40 mL) was stirred at 70° C. for 12 hours. To the resulting mixture was added water, and the resulting mixture was extracted with chloroform. The resulting organic layer was washed with saturated brine, dried over anhydrous sodium sulfate, and concentrated under reduced pressure. The resulting residue was subjected to silica gel chromatography to give the Intermediate compound (3) represented by the following formula (2.75 g).

Intermediate compound (3)

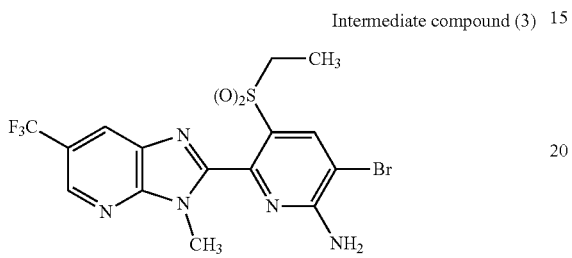

$^1$H-NMR (CDCl$_3$) δ: 8.74 (1H, s), 8.39 (1H, s), 8.29 (1H, s), 5.69 (2H, br s), 3.85 (3H, s), 3.64 (2H, q, J=7.5 Hz), 1.33 (3H, t, J=7.5 Hz).

Reference Preparation Example 2-2

The compound prepared according to the method described in the Reference Preparation Example 2-1 and the physical property thereof are shown below.

Intermediate compound (4)

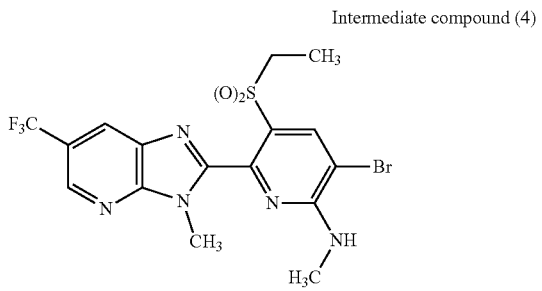

$^1$H-NMR (CDCl$_3$) δ: 8.75 (1H, d, J=2.1 Hz), 8.32 (1H, s), 8.30 (1H, d, J=2.1 Hz), 5.80 (1H, d, J=5.0 Hz), 3.90 (3H, s), 3.70 (2H, q, J=7.4 Hz), 3.10 (3H, d, J=5.0 Hz), 1.35 (3H, t, J=7.4 Hz).

Reference Preparation Example 3

To a mixture of the Intermediate compound (3) (1.9 g), di-tert-butyl dicarbonate (1.8 g), and THF (16 mL) was added triethylamine (1.1 mL), and the resulting mixture was stirred at 70° C. for 24 hours. To the resulting mixture was added water, and the resulting mixture was extracted with chloroform. The resulting organic layer was washed with saturated brine, dried over anhydrous sodium sulfate, and concentrated under reduced pressure to give the Intermediate compound (9) represented by the following formula (2.75 g).

Intermediate compound (9)

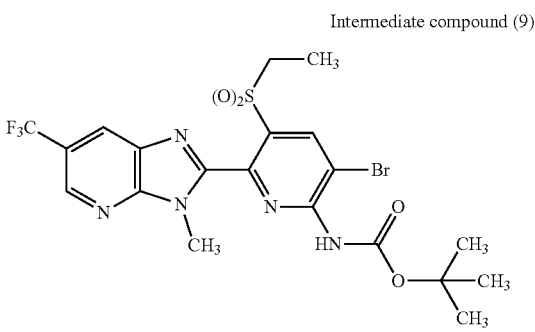

$^1$H-NMR (CDCl$_3$) δ: 8.75 (1H, s), 8.61 (1H, s), 8.28 (1H, s), 7.66 (1H, s), 4.08 (3H, s), 4.01 (2H, q, J=7.5 Hz), 1.53 (9H, s), 1.41 (3H, t, J=7.5 Hz).

Reference Preparation Example 4-1

A mixture of 2-[5-bromo-3-(ethanesulfonyl)pyridin-2-yl]-3-methyl-6-(trifluoromethyl)-3H-imidazo[4,5-b]pyridine (9.0 g), bis(pinacolato)diboron (5.6 g), [1,1'-bis(diphenylphosphino)ferrocene]palladium(II) dichloride·dichloromethane adduct (0.49 g), potassium acetate (5.9 g), and DMSO (80 mL) was stirred under nitrogen atmosphere at 90° C. for 10 hours. To the resulting mixture was added water at room temperature, and the resulting mixture was extracted with chloroform. The resulting organic layer was washed with saturated brine, dried over anhydrous magnesium sulfate, and concentrated under reduced pressure to give the Intermediate compound (5) represented by the following formula (8.1 g).

Intermediate compound (5)

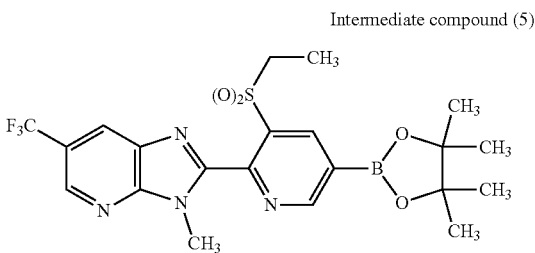

$^1$H-NMR (CDCl$_3$) δ: 9.27 (1H, d, J=1.4 Hz), 8.87 (1H, d, J=1.4 Hz), 8.76 (1H, d, J=1.8 Hz), 8.31 (1H, d, J=1.8 Hz), 3.87 (3H, s), 3.82 (2H, q, J=7.5 Hz), 1.42 (12H, s), 1.38 (3H, t, J=7.5 Hz).

Reference Preparation Example 4-2

The compound prepared according to the method described in the Reference Preparation Example 4-1 and the physical property thereof are shown below.

Intermediate compound (6)

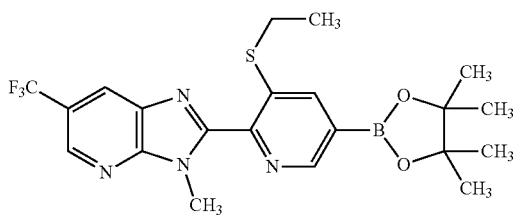

¹H-NMR (CDCl₃) δ: 8.83 (1H, d, J=1.4 Hz), 8.73 (1H, d, J=1.4 Hz), 8.41-8.39 (1H, m), 8.14-8.12 (1H, m), 4.02 (3H, s), 3.02 (2H, q, J=7.5 Hz), 1.40 (12H, s), 1.34 (3H, t, J=7.5 Hz).

Intermediate compound (7)

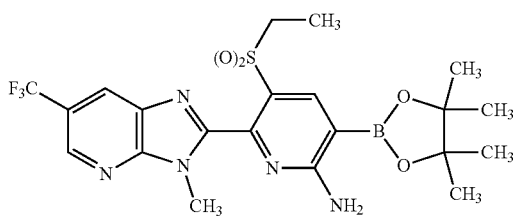

¹H-NMR (CDCl₃) δ: 8.72 (1H, d, J=1.4 Hz), 8.54 (1H, s), 8.28 (1H, d, J=1.4 Hz), 3.83 (3H, s), 3.56 (2H, q, J=7.5 Hz), 1.39 (12H, s), 1.32 (3H, t, J=7.5 Hz).

Intermediate compound (8)

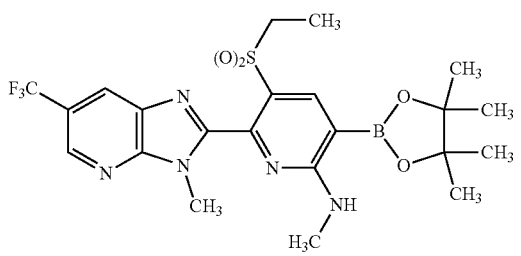

¹H-NMR (CDCl₃) δ: 8.78 (1H, d, J=1.4 Hz), 8.34 (1H, d, J=1.4 Hz), 8.09 (1H, s), 5.09 (1H, s), 4.01 (3H, s), 3.75 (2H, q, J=7.4 Hz), 3.07 (3H, d, J=4.8 Hz), 1.39 (3H, t, J=7.4 Hz), 1.24 (12H, s).

Preparation Example 1-1

A mixture of the Intermediate compound (5) (0.30 g), 2-chloro-5-cyanopyridine (0.084 g), [1,1'-bis(diphenylphosphino)ferrocene]palladium(II) dichloride•dichloromethane adduct (0.0099 g), tripotassium phosphate (0.385 g), 1,2-dimethoxyethane (4 mL), and water (0.4 mL) was stirred under nitrogen atmosphere at 80° C. for 4 hours. To the resulting mixture was added water at room temperature, and the resulting mixture was extracted with ethyl acetate. The resulting organic layer was washed with saturated brine, dried over anhydrous magnesium sulfate, and concentrated under reduced pressure. The resulting residue was subjected to silica gel chromatography (hexane:ethyl acetate=2:1) to give the Present compound 1 represented by the following formula (0.21 g).

Present compound 1

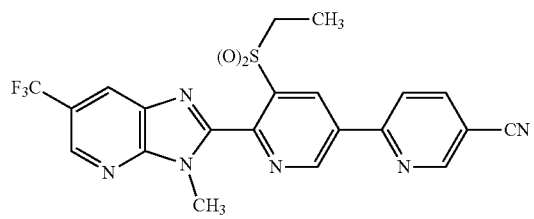

¹H-NMR (CDCl₃) δ: 9.67 (1H, d, J=2.0 Hz), 9.16 (1H, d, J=2.0 Hz), 9.10-9.07 (1H, m), 8.81-8.77 (1H, m), 8.36-8.33 (1H, m), 8.21 (1H, dd, J=8.3, 2.2 Hz), 8.10 (1H, dd, J=8.4, 0.9 Hz), 3.95 (3H, s), 3.95 (2H, q, J=7.4 Hz), 1.43 (3H, t, J=7.4 Hz).

Preparation Example 1-2

The compound prepared according to the method described in the Preparation Example 1-1 and the physical property thereof are shown below.

Present compound 2

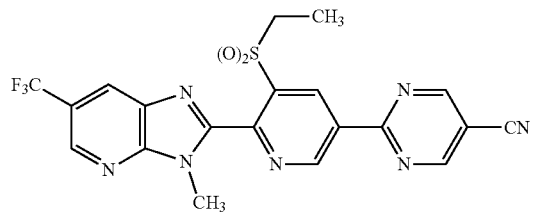

¹H-NMR (CDCl₃) δ: 10.02 (1H, d, J=2.0 Hz), 9.56 (1H, d, J=2.0 Hz), 9.19 (2H, s), 8.79 (1H, d, J=1.8 Hz), 8.34 (1H, d, J=1.8 Hz), 3.97 (3H, s), 3.95 (2H, q, J=7.5 Hz), 1.44 (3H, t, J=7.5 Hz).

Present compound 3

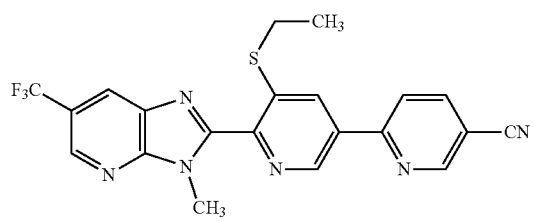

¹H-NMR (CDCl₃) δ: 9.08-9.06 (1H, m), 9.03 (1H, dd, J=2.1, 0.7 Hz), 8.76 (1H, d, J=1.4 Hz), 8.54-8.53 (1H, m), 8.43 (1H, d, J=1.4 Hz), 8.14 (1H, dd, J=8.2, 2.1 Hz), 8.00 (1H, dd, J=8.2, 0.7 Hz), 4.12 (3H, s), 3.10 (2H, q, J=7.3 Hz), 1.42 (3H, t, J=7.3 Hz).

Present compound 4

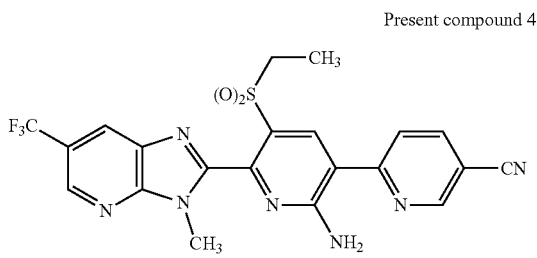

¹H-NMR (CDCl₃) δ: 8.91-8.90 (1H, m), 8.69 (1H, d, J=1.4 Hz), 8.62 (1H, s), 8.25 (1H, d, J=1.4 Hz), 8.11 (1H, d, J=8.2 Hz), 8.06 (1H, d, J=8.2 Hz), 3.86 (3H, s), 3.67 (2H, q, J=7.5 Hz), 1.31 (3H, t, J=7.5 Hz).

Present compound 5

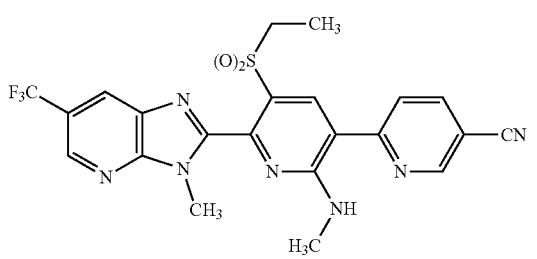

¹H-NMR (CDCl₃) δ: 8.78-8.75 (1H, m), 8.68-8.66 (1H, m), 8.35-8.30 (2H, m), 7.89 (1H, dd, J=8.8, 2.3 Hz), 7.69 (1H, d, J=9.1 Hz), 7.39 (1H, d, J=8.8 Hz), 3.88 (3H, s), 3.76-3.70 (5H, m), 1.37 (3H, t, J=7.5 Hz).

Present compound 6

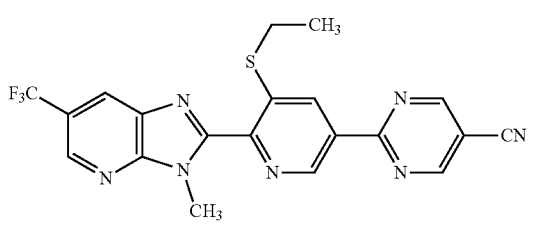

¹H-NMR (CDCl₃) δ: 9.82 (1H, d, J=2.0 Hz), 9.55 (1H, d, J=2.0 Hz), 9.15 (2H, s), 8.61-8.59 (1H, m), 8.44-8.43 (1H, m), 4.15 (3H, s), 3.19 (2H, q, J=7.4 Hz), 1.43 (3H, t, J=7.4 Hz).

Present compound 7

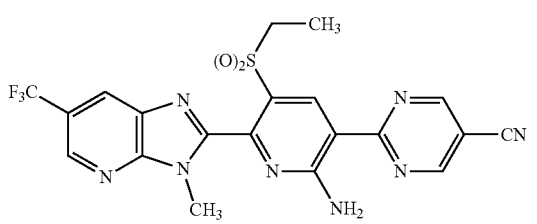

¹H-NMR (CDCl₃) δ: 9.56 (1H, s), 9.13 (2H, s), 8.76 (1H, d, J=1.4 Hz), 8.31 (1H, d, J=1.4 Hz), 6.17 (2H, s), 3.93 (3H, s), 3.70 (2H, q, J=7.4 Hz), 1.38 (3H, t, J=7.4 Hz).

Preparation Example 2-1

A mixture of the Present compound 3 (0.26 g), mCPBA (0.072 g), and chloroform (3 mL) was stirred at room temperature for 4 hours. To the resulting mixture was added an aqueous solution of sodium thiosulfate at room temperature, the resulting mixture was stirred for 1 hour, and then extracted with chloroform. The resulting organic layer was washed sequentially with a saturated aqueous solution of sodium hydrogen carbonate and saturated brine, dried over anhydrous magnesium sulfate, and concentrated under reduced pressure. The resulting residue was subjected to silica gel chromatography (hexane:ethyl acetate=3:1) to give the Present compound 8 represented by the following formula (0.081 g).

Present compound 8

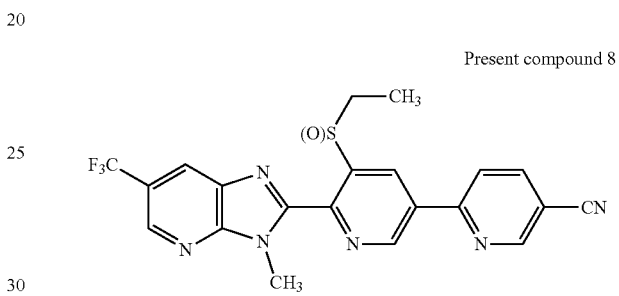

¹H-NMR (CDCl₃) δ: 9.63-9.60 (1H, m), 9.22-9.19 (1H, m), 9.07-9.05 (1H, m), 8.81-8.79 (1H, m), 8.39-8.37 (1H, m), 8.16 (1H, dd, J=8.4, 2.0 Hz), 8.13 (1H, dd, J=8.4, 1.0 Hz), 4.43 (3H, s), 3.78-3.69 (1H, m), 3.18-3.09 (1H, m), 1.52 (3H, t, J=7.5 Hz).

Preparation Example 2-2

The compound prepared according to the method described in the Preparation Example 2-1 and the physical property thereof are shown below.

Present compound 9

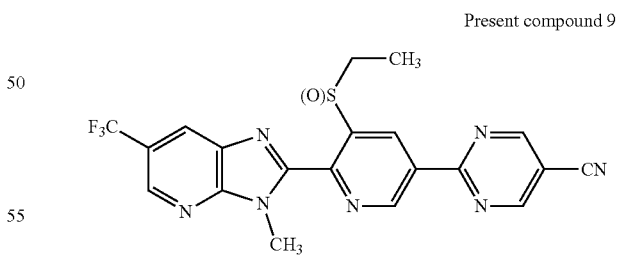

¹H-NMR (CDCl₃) δ: 9.88 (1H, d, J=2.0 Hz), 9.68 (1H, d, J=2.0 Hz), 9.16 (2H, s), 8.81 (1H, d, J=1.6 Hz), 8.38 (1H, d, J=1.6 Hz), 4.44 (3H, s), 3.75-3.70 (1H, m), 3.18-3.11 (1H, m), 1.52 (3H, t, J=7.5 Hz).

Next, examples of the Present compounds prepared according to any one of the Preparation Examples described in Examples and the processes described in the present description are shown below.

A compound represented by formula (I)

$$\text{(I)}$$

[Structure: F$_3$C-substituted imidazo[4,5-b]pyridine with N-CH$_3$, connected to a pyridine bearing S(O)$_n$CH$_3$ and R$^1$, linked to another pyridine with A and CN]

wherein A represents a CH, n represents 2, and R$^1$ represents any one substituent described in [Table 1](hereinafter referred to as "Compound group SX1").

TABLE 1

| |
|---|
| H |
| NH$_2$ |
| NHCH$_3$ |
| NHCH$_2$CH$_3$ |
| NHCH$_2$CH$_2$CH$_3$ |
| N(CH$_3$)$_2$ |
| N(CH$_3$)CH$_2$CH$_3$ |
| NHCH(CH$_3$)$_2$ |
| NHC(CH$_3$)$_3$ |
| N(CH$_2$CH$_3$)$_2$ |
| N(CH$_2$CH$_2$CH$_3$)$_2$ |

A compound represented by formula (I), wherein A represents a N, n represents 2, and R$^1$ represents any one substituent described in [Table 1] (hereinafter referred to as "Compound group SX2").

A compound represented by formula (I), wherein A represents a CH, n represents 1, and R$^1$ represents any one substituent described in [Table 1] (hereinafter referred to as "Compound group SX3").

A compound represented by formula (I), wherein A represents a N, n represents 1, and R$^1$ represents any one substituent described in [Table 1] (hereinafter referred to as "Compound group SX4").

A compound represented by formula (I), wherein A represents a CH, n represents 0, and R$^1$ represents any one substituent described in [Table 1] (hereinafter referred to as "Compound group SX5").

A compound represented by formula (I), wherein A represents a N, n represents 0, and R$^1$ represents any one substituent described in [Table 1] (hereinafter referred to as "Compound group SX6").

Next, examples of compounds prepared according to any one of Examples or Reference processes are shown below.
A compound represented by formula (L-1)

$$\text{(L-1)}$$

[Structure similar to (I) but with Z$^1$ in place of R$^1$]

wherein A represents a CH, n represents 2, and Z$^1$ represents any one substituent described in [Table 2].

TABLE 2

| |
|---|
| NHC(O)CH$_3$ |
| NHC(O)CH$_2$CH$_3$ |
| NHC(O)CH$_2$CH$_2$CH$_3$ |
| NHC(O)CH(CH$_3$)$_2$ |
| N(CH$_3$)C(O)CH$_3$ |
| N(CH$_3$)C(O)CH$_2$CH$_3$ |
| N(CH$_3$)C(O)CH$_2$CH$_2$CH$_3$ |
| N(CH$_3$)C(O)CH(CH$_3$)$_2$ |
| NHC(O)OCH$_3$ |
| NHC(O)OCH$_2$CH$_3$ |
| NHC(O)OCH$_2$CH$_2$CH$_3$ |
| NHC(O)OCH(CH$_3$)$_2$ |
| N(CH$_3$)C(O)OCH$_3$ |
| N(CH$_3$)C(O)OCH$_2$CH$_3$ |
| N(CH$_3$)C(O)OCH$_2$CH$_2$CH$_3$ |
| N(CH$_3$)C(O)OCH(CH$_3$)$_2$ |
| N=CHN(CH$_3$)$_2$ |

$$N{=}\overset{H}{\underset{|}{C}}{-}\!\!\left\langle\!\!\!\bigcirc\!\!\!\right\rangle\!\!{-}OCH_3$$

A compound represented by formula (L-1), wherein A represents a N, n represents 2, and Z$^1$ represents any one substituent described in [Table 2].

A compound represented by formula (L-1), wherein A represents a CH, n represents 1, and Z$^1$ represents any one substituent described in [Table 2].

A compound represented by formula (L-1), wherein A represents a N, n represents 1, and Z$^1$ represents any one substituent described in [Table 2].

A compound represented by formula (L-1), wherein A represents a CH, n represents 0, and Z$^1$ represents any one substituent described in [Table 2].

A compound represented by formula (L-1), wherein A represents a N, n represents 0, and Z$^1$ represents any one substituent described in [Table 2].

Next, the Formulation Examples of the Present compound are shown below. The "part(s)" represents "part(s) by weight".

Formulation Example 1

Any one of the Present compounds 1 to 9 (10 parts) is mixed with a mixture of xylene (35 parts) and DMF (35 parts), and then polyoxyethylene styryl phenyl ether (14 parts) and calcium dodecylbenzene sulfonate (6 parts) are added thereto, followed by mixing them to obtain each formulation.

Formulation Example 2

Sodium lauryl sulfate (4 parts), calcium lignin sulfonate (2 parts), wet silica (20 parts), and diatomaceous earth (54 parts) are mixed, and further any one of the Present compounds 1 to 9 (20 parts) is added thereto, followed by mixing them to obtain each formulation.

Formulation Example 3

To any one of the Present compounds 1 to 9 (2 parts) are added wet silica (1 part), calcium lignin sulfonate (2 parts), bentonite (30 parts), and kaolin clay (65 parts), followed by mixing them to obtain a mixture. To the mixture is then added an appropriate amount of water, the resulting mixture

Formulation Example 4

Any one of the Present compounds 1 to 9 (1 part) is mixed with an appropriate amount of acetone, and then wet silica (5 parts), acidic isopropyl phosphate (0.3 part), and kaolin clay (93.7 parts) are added thereto, followed by mixing with stirring thoroughly and removal of acetone from the mixture by evaporation to obtain each formulation.

Formulation Example 5

A mixture of polyoxyethylene alkyl ether sulfate ammonium salt and wet silica (weight ratio of 1:1) (35 parts), any one of the Present compounds 1 to 9 (20 parts), and water (45 parts) are thoroughly mixed to obtain each formulation.

Formulation Example 6

Any one of the Present compounds 1 to 9 (0.1 part) is mixed with a mixture of xylene (5 parts) and trichloroethane (5 parts), and the resulting mixture is then mixed with kerosene (89.9 parts) to obtain each formulation.

Formulation Example 7

Any one of the Present compounds 1 to 9 (10 mg) is mixed with acetone (0.5 mL), and the solution is added dropwise to a solid feed powder for an animal (solid feed powder for rearing and breeding CE-2, manufactured by CLEA Japan, Inc.) (5 g), followed by mixing the resulting mixture uniformly, and then by drying it by evaporation of acetone to obtain each poison bait.

Formulation Example 8

Any one of the Present compounds 1 to 9 (0.1 part) and Neothiozole (manufactured by Chuo Kasei Co., Ltd.) (49.9 parts) are placed into an aerosol can. After mounting an aerosol valve, dimethyl ether (25 parts) and LPG (25 parts) are filled, followed by shaking and further mounting an actuator to obtain each oily aerosol.

Formulation Example 9

A mixture of any one of the Present compounds 1 to 9 (0.6 part), 2,6-di-tert-butyl-4-methylphenol (0.01 part), xylene (5 parts), kerosene (3.39 parts), and Rheodol (registered trademark) MO-60 (1 part), and distilled water (50 parts) are filled into an aerosol container, and a valve part is attached. Then, LPG (40 parts) is filled therein through the valve to obtain each aqueous aerosol.

Formulation Example 10

Any one of the Present compounds 1 to 9 (0.1 g) is mixed with propylene glycol (2 mL), and the resulting solution is impregnated into a ceramic plate having a size of 4.0 cm×4.0 cm and a thickness of 1.2 cm to obtain each thermal smoking agent.

Formulation Example 11

Any one of the Present compounds 1 to 9 (5 parts) and ethylene-methyl methacrylate copolymer (the ratio of the methyl methacrylate relative to the total weight of the copolymer: 10% by weight) (95 parts) are melted and kneaded, and the resulting kneaded product is extruded from an extrusion molding machine to obtain each rod-shaped molded product having a length of 15 cm and a diameter of 3 mm.

Formulation Example 12

Any one of the Present compounds 1 to 9 (5 parts) and flexible vinyl chloride resin (95 parts) are melted and kneaded, and the resulting kneaded product is extruded from an extrusion molding machine to obtain each rod-shaped molded product having a length of 15 cm and a diameter of 3 mm.

Formulation Example 13

Any one of the Present compounds 1 to 9 (100 mg), lactose (68.75 mg), corn starch (237.5 mg), microcrystalline cellulose (43.75 mg), polyvinylpyrrolidone (18.75 mg), sodium carboxymethyl starch (28.75 mg), and magnesium stearate (2.5 mg) are mixed, and the resulting mixture is compressed to an appropriate size to obtain each tablet.

Formulation Example 14

Any one of the Present compounds 1 to 9 (25 mg), lactose (60 mg), corn starch (25 mg), carmellose calcium (6 mg), and an appropriate amount of 5% hydroxypropyl methylcellulose are mixed, and the resulting mixture is filled into a hard shell gelatin capsule or a hydroxypropyl methylcellulose capsule to obtain each capsule.

Formulation Example 15

To any one of the Present compounds 1 to 9 (100 mg), fumaric acid (500 mg), sodium chloride (2,000 mg), methylparaben (150 mg), propylparaben (50 mg), granulated sugar (25,000 mg), sorbitol (70% solution) (13,000 mg), Veegum (registered trademark) K (100 mg), perfume (35 mg), and colorant (500 mg) is added distilled water so that the final volume is set to be 100 mL, followed by mixing them to obtain each suspension for oral administration.

Formulation Example 16

Any one of the Present compounds 1 to 9 (5 parts) is mixed with an emulsifier (5 parts), benzyl alcohol (3 parts), and propylene glycol (30 parts), and phosphate buffer is added thereto so that the pH of the solution is set to be 6.0 to 6.5, and then water is added thereto as the rest parts to obtain each solution for oral administration.

Formulation Example 17

Aluminum distearate (5 parts) is added to fractional distilled coconut oil (57 parts) and polysorbate 85 (3 parts), and dispersed by heating. The resulting mixture is cooled to room temperature, and saccharin (25 parts) is dispersed in the oil vehicle. Any one of the Present compounds 1 to 9 (10 parts) is distributed thereto to obtain each paste-like formulation for oral administration.

Formulation Example 18

Any one of the Present compounds 1 to 9 (5 parts) is mixed with a limestone filler (95 parts), followed by a wet granulation of the resulting mixture to obtain each granule for oral administration.

Formulation Example 19

Any one of the Present compounds 1 to 9 (5 parts) is mixed with diethylene glycol monoethyl ether (80 parts), propylene carbonate (15 parts) is added thereto, and the resulting mixture is mixed to obtain each spot-on formulation.

Formulation Example 20

Any one of the Present compounds 1 to 9 (10 parts) is mixed with diethylene glycol monoethyl ether (70 parts), 2-octyldodecanol (20 parts) is added thereto, and the resulting mixture is mixed to obtain each pour-on formulation.

Formulation Example 21

Any one of the Present compounds 1 to 9 (0.1 part), sodium polyoxyethylene lauryl ether sulfate (25% aqueous solution) (40 parts), lauramidopropyl betaine (5 parts), coconut oil fatty acid ethanolamide (5 parts), carboxyvinyl polymer (0.5 part), and purified water (49.4 parts) are thoroughly mixed to obtain each shampoo formulation.

Formulation Example 22

Any one of the Present compounds 1 to 9 (0.15 part), an animal feed (95 parts), and a mixture (4.85 parts) consisting of calcium hydrogen phosphate, diatomaceous earth, Aerosil (registered trademark), and carbonate (or chalk) are mixed with stirring thoroughly to obtain each premix for an animal feed.

Formulation Example 23

Any one of the Present compounds 1 to 9 (7.2 g) and Hosco (registered trademark) S-55 (92.8 g) are mixed at 100° C., and the resulting mixture is poured into a suppository mold, followed by performing a cooling solidification to obtain each suppository.

Formulation Example 24

An aqueous solution (28 parts) comprising any one of the Present compounds 1 to 9 (10 parts), sorbitan trioleate (1.5 parts), and polyvinyl alcohols (2 parts) are mixed and finely ground by a wet grinding method. An aqueous solution comprising xanthane gum (0.05 part) and aluminum magnesium silicate (0.1 part) are added thereto to obtain a mixture (total amount: 90 parts), further propylene glycol (10 parts) is added thereto, and the resulting mixture is stirred to obtain each formulation.

Formulation Example 25

Any one of the Present compounds 1 to 9 (10 parts), talc (10 parts), and kaolin clay (80 parts) are fully mixed and ground to obtain each formulation.

Formulation Example 26

Any one of the Present compounds 1 to 9 (10 parts) and diethylene glycol monoethyl ether (90 parts) are thoroughly mixed to obtain each formulation.

Formulation Example 27

Any one of the Present compounds 1 to 9 (10 parts), N-octylpyrrolidone (5 parts), and N-methylpyrrolidone (85 parts) are thoroughly mixed to obtain each formulation.

Formulation Example 28

Any one of the Present compounds 1 to 9 (10 parts), DMF (7 parts), and macrogol 400 (83 parts) are thoroughly mixed to obtain each formulation.

Formulation Example 29

Any one of the Present compounds 1 to 9 (10 parts), DMF (7 parts), and propylene carbonate (83 parts) are thoroughly mixed to obtain each formulation.

Formulation Example 30

Any one of the Present compounds 1 to 9 (10 parts), corn starch (20 parts), flavor (4.5 parts), aspartame (0.5 part), magnesium stearate (2 parts), macrogol 3350 (5 parts), glycerin (5 parts), sodium lauryl sulfate (5 parts), sodium pamoate (1 part), soybean oil (6 parts), and sucrose (40 parts) are thoroughly mixed, and the resulting mixture is tabletted to obtain each tablet.

Formulation Example 31

Any one of the Present compounds 1 to 9 (10 parts), macrogol 400 (6 parts), macrogol 4000 (20 parts), macrogol 15 hydroxystearate (2 parts), glycerin (4 parts), povidone (5 parts), soy protein (5 parts), medium-chain triglyceride (13 parts), flavor (10 parts), and corn starch (25 parts) are thoroughly mixed, the resulting mixture is poured into a mold, and taken out of the mold to obtain each chewable tablet.

Formulation Example 32

Any one of the Present compounds 1 to 9 (10 parts), triethyl phosphate (10 parts), diisodecyl adipate (15 parts), isostearic acid (2.3 parts), erucic acid (2.5 parts), epoxidized soybean oil (2.3 parts), and barium/zinc liquid stabilizer (1.1 parts) are mixed at room temperature to prepare a homogeneous mixed liquid. Next, barium stearate (0.2 part) and vinyl chloride resin (56.6 parts) are put into a kneader kept at approximately 170° C. to obtain a mixture, and the above mixed liquid is gradually added thereto with kneading the mixture. Then, the resulting mixture is further kneaded to obtain each resin composition A.

Formulation Example 33

A resin composition A is molded into a sheet-shape by a press machine kept at approximately 180° C., and the resulting sheet-shaped molded product is pelletized by a sheet pelletizer. The resulting pellet is subjected to injection molding at 180° C. to obtain a molded product having a shape of animal collar (collar formulation).

Formulation Example 34

To any one of the Present compounds 1 to 9 (7.5 parts) is added low substituted hydroxypropylcellulose (15 parts) to obtain a mixed powder. Silicone A ingredient (35 parts) and Silicone B ingredient (42.5 parts) of SILASTIC (registered trademark) Q7-4750 manufactured by Dow Corning Corporation are thoroughly mixed, and the above mixed powder is quickly added thereto, followed by mixing them to obtain a mixture. Then, the resulting mixture is extended by a two-roll, and hardened at 40° C. for 1 day to obtain each sheet formulation. The resulting sheet formulation is cut to obtain each implant tablet.

Next, Test Examples are used to show effects of the Present compounds on harmful arthropods. In the following Test Examples, the tests were carried out at 25° C.

Test Method 1

Each test compound is formulated according to the process described in the Formulation Example 5 to obtain each formulation, and water containing Sindaine (registered trademark) (0.03% by volume) is added thereto to prepare a diluted solution containing a prescribed concentration of each test compound.

Cucumber (*Cucumis sativus*) seedlings (on the developmental stage of the second true leaf) are planted in a container and approximately 30 cotton aphids (*Aphis gossypii*) (all stages of life) are released onto the cucumber seedlings. After 1 day, each of said diluted solutions is sprayed into the seedlings in a ratio of 10 mL/seedling. After additional 5 days, the number of the surviving insects is examined and the controlling value is calculated by the following equation.

Controlling value(%)={1−($Cb \times Tai$)/($Cai \times Tb$)}×100 wherein the symbols in the equation represent the following meanings.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group Here the "untreated group" represents a group where a similar treatment procedure to that of the treated group except not using each test compound is done.

Test Example 1-1

When the prescribed concentration was 500 ppm and each of the following Present compounds was used as a test compound to carry out a test according to the Test method 1, each of the following Present compounds showed 90% or greater as the controlling value.
Present compounds: 1, 2, 4, 5, 7, 8, and 9

Test Example 1-2

When the prescribed concentration was 200 ppm and each of the following Present compounds was used as a test compound to carry out a test according to the Test method 1, each of the following Present compounds showed 90% or greater as the controlling value.

Present compounds: 1, 2, 4, 7, and 8

Test Method 2

Each test compound is formulated according to the process described in the Formulation Example 5 to obtain each formulation, and water is added thereto to prepare a diluted solution containing a prescribed concentration of each test compound.

Cucumber seedlings (on the developmental stage of the second true leaf) are planted in a container, and each of said diluted solutions is irrigated into the plant foot in a ratio of 5 mL/seedling. After 7 days, approximately 30 cotton aphids (*Aphis gossypii*) (all stages of life) are released onto the surfaces of leaves of the cucumber seedlings. After additional 6 days, the number of the surviving insects is examined and the controlling value is calculated by the following equation.

Controlling value(%)={1−($Cb \times Tai$)/($Cai \times Tb$)}×100 wherein the symbols in the equation represent the following meanings.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group Here the "untreated group" represents a group where a similar treatment procedure to that of the treated group except not using each test compound is done.

Test Example 2

When the prescribed concentration was 1000 ppm and each of the following Present compounds was used as a test compound to carry out a test according to the Test method 2, each of the following Present compounds showed 90% or greater as the controlling value.
Present compounds: 1, 2, and 7

Test Method 3

Each test compound is formulated according to the process described in the Formulation Example 5 to obtain each formulation, and water containing Sindaine (registered trademark) (0.03% by volume) is added thereto to prepare a diluted solution containing a prescribed concentration of each test compound.

Rice (*Oryza sativa*) seedlings (on the developmental stage of the second true leaf) are planted in a container, and each of said diluted solutions is sprayed into the seedlings in a ratio of 10 mL/seedling. Thereafter, 20 the 3rd instar larvae of brown planthopper (*Nilaparvata lugens*) are released onto the rice seedlings. After 6 days, the number of the surviving insects is examined and the mortality of insects is calculated by the following equation.

Mortality(%)={1−Number of surviving insects/20}×100

Test Example 3

When the prescribed concentration was 500 ppm and each of the following Present compounds was used as a test compound to carry out a test according to the Test method 3, each of the following Present compounds showed 90% or greater as the controlling value.
Present compounds: 1 and 2
Test Method 4

Each test compound is formulated according to the process described in the Formulation Example 5 to obtain each formulation, and water is added thereto to prepare a diluted solution containing a prescribed concentration of each test compound.

An artificial diet (Insecta LF, manufactured by Nosan Corporation) (7.7 g) is placed in a container, and thereto is irrigated each of said diluted solutions (2 mL). Five (5) the 4th instar larvae of cotton worm (*Spodoptera litura*) are released onto the artificial diet. After 5 days, the number of the surviving insects is counted, and the mortality of insects is calculated by the following equation.

Mortality(%)=(1−Number of surviving insects/5)× 100

Test Example 4

When the prescribed concentration was 500 ppm and each of the following Present compounds was used as a test compound to carry out a test according to the Test method 4, each of the following Present compounds showed 80% or greater as the mortality.
Present compounds: 1, 2, 4, and 7
Test Method 5

Each test compound is formulated according to the process described in the Formulation Example 5 to obtain each formulation, and water containing Sindaine (registered trademark) (0.03% by volume) is added thereto to prepare a diluted solution containing a prescribed concentration of each test compound.

Cabbage (*Brassicae oleracea*) seedlings (on the developmental stage of the second to third true leaf) are planted in a container, and each of said diluted solutions is sprayed into the seedlings in a ratio of 20 mL/seedling. Thereafter, the stem and leaf of the seedlings are cut out, and placed into a container lined with a filter paper. Five(5) the 2nd instar larvae of diamondback moth (*Plutella xylostella*) are released into the container. After 5 days, the number of the surviving insects is counted, and the mortality of insects is calculated by the following equation.

Mortality(%)=(1−Number of surviving insects/ 5)×100

Test Example 5

When the prescribed concentration was 500 ppm and each of the following Present compounds was used as a test compound to carry out a test according to the Test method 5, each of the following Present compounds showed 80% or greater as the mortality.
Present compounds: 1, 2, 3, 4, 5, 6, and 7
Test Method 6

Each test compound is formulated according to the process described in the Formulation Example 5 to obtain each formulation, and water containing Sindaine (registered trademark) (0.03% by volume) is added thereto to prepare a diluted solution containing a prescribed concentration of each test compound.

Cabbage seedlings (on the developmental stage of the third to fourth true leaf) are planted in a container, and each of said diluted solutions is sprayed into the seedlings in a ratio of 20 mL/seedling. Thereafter, 10 the 3rd instar larvae of diamondback moth (*Plutella xylostella*) are released into the cabbage seedlings. After 5 days, the number of the surviving insects is counted, and the mortality of insects is calculated by the following equation.

Mortality(%)=(1−Number of surviving insects/ 10)×100

Test Example 6

When the prescribed concentration was 200 ppm and each of the following Present compounds was used as a test compound to carry out a test according to the Test method 6, each of the following Present compounds showed 90% or greater as the mortality.
Present compounds: 1, 2, 4, and 7
Test Method 7

Each test compound is dissolved into a mixed solution (50 μL) of polyoxyethylene sorbitan mono-cocoate and acetone (at a volume ratio of polyoxyethylene sorbitan mono-cocoate:acetone=5:95) per 1 mg of the test compound. Water containing Sindaine (registered trademark) (0.03% by volume) is added thereto to prepare a diluted solution containing a prescribed concentration of each test compound.

Corns (*Zea mays*) are inoculated onto a tray lined with wet Kimwipes. After the corns are grown for 5 days, the entire seedlings of the corns are immersed into each of said diluted solutions for 30 seconds. Thereafter, two seedlings are placed into a petri dish (diameter: 90 mm), and 10 the 2nd instar larvae of western corn rootworm (*Diabrotica virgifera virgifera*) are released into the dish. After 5 days, the number of the dead insects is counted, and the mortality of insects is calculated by the following equation.

Mortality(%)=(Number of dead insects/10)×100

Test Example 7-1

When the prescribed concentration was 500 ppm and each of the following Present compounds was used as a test compound to carry out a test according to the Test method 7, each of the following Present compounds showed 80% or greater as the mortality.
Present compounds: 1, 4, 5, 7, and 8

Test Example 7-2

When the prescribed concentration was 50 ppm and each of the following Present compounds was used as a test compound to carry out a test according to the Test method 7, each of the following Present compounds showed 80% or greater as the mortality.
Present compounds: 1, 4, and 5
Test Method 8

Each test compound is formulated according to the process described in the Formulation Example 5 to obtain each formulation, and water is added thereto to prepare a diluted solution containing a prescribed concentration of each test compound.

A filter paper having a diameter of 5.5 cm is lined with the inside bottom of a cup having a diameter of 5.5 cm, each of said diluted solutions (0.7 mL) is added dropwise on the filter paper, and sucrose (30 mg) is homogeneously placed into said cup as a feed. Ten(10) female adult house flies (*Musca domestica*) are released into said cup, and the cup is covered. After 24 hours, life and death of the house flies are examined, the number of the dead insects is counted, and the mortality of insects is calculated by the following equation.

Mortality(%)=(Number of dead insects/Number of test insects)×100

Test Example 8-1

When the prescribed concentration was 500 ppm and each of the following Present compounds was used as a test compound to carry out a test according to the Test method 8, each of the following Present compounds showed 100% as the mortality.
Present compounds: 1, 2, and 7

Test Example 8-2

When the prescribed concentration was 125 ppm and each of the following Present compounds was used as a test compound to carry out a test according to the Test method 8, each of the following Present compounds showed 100% as the mortality.
Present compounds: 1, 2, and 4
Test Method 9

Each test compound is formulated according to the process described in the Formulation Example 5 to obtain each formulation, and water is added thereto to prepare a diluted solution containing a prescribed concentration of each test compound.

A filter paper having a diameter of 5.5 cm is lined with the inside bottom of a cup having a diameter of 5.5 cm, each of said diluted solutions (0.7 mL) is added dropwise on the filter paper, and sucrose (30 mg) is homogeneously placed into said cup as a feed. Two(2) male adult German cockroaches (*Blattella germanica*) are released into said cup, and the cup is covered. After 6 days, life and death of the German cockroach are examined, the number of the dead insects is counted, and the mortality of insects is calculated by the following equation.

Mortality(%)=(Number of dead insects/Number of test insects)×100

Test Example 9

When the prescribed concentration was 500 ppm and each of the following Present compounds was used as a test compound to carry out a test according to the Test method 9, each of the following Present compounds showed 100% as the mortality.
Present compounds: 1, 2, and 7

Test Example 10

A mixed solution of the Present compound 1, 3, or 6 (1 mg) and acetone (0.2 mL) was placed into a screw tube (27×55 mm), the entire inner wall was homogeneously coated with said solution, and then air-dried. Five(5) young mites (*Haemaphysalis longicornis*) before blood-sucking were released into the screw tube, and the tube was covered. After 2 days, the number of the dead insects is counted, and the mortality of insects was calculated by the following equation.

Mortality(%)=100×(Number of dead insects/Number of test insects)

As a result, each treated group wherein a test drug solution comprising the Present compound 1, 3, or 6 was used showed 80% or greater as the mortality.

Test Example 11

The Present compound (1 mg) is dissolved into a mixed solution (10 µL) of xylene, DMF, and surfactant (at a volume ratio of xylene:DMF:surfactant=4:4:1), and the resulting solution is diluted with water containing a spreader (0.02% by volume) to prepare a diluted solution A containing a prescribed concentration of the Present compound.

The Present ingredient (1 mg) is dissolved into a mixed solution (10 µL) of xylene, DMF, and surfactant (at a volume ratio of xylene:DMF:surfactant=4:4:1), and the resulting solution is diluted with water containing a spreader (0.02% by volume) to prepare a diluted solution B containing a prescribed concentration of the Present ingredient.

The diluted solution A and the diluted solution B are mixed to prepare a diluted solution C.

A lamina (length: 1.5 cm) of cucumber cotyledon is placed into each well of a 24 well microplate, then two(2) wingless adults and eight(8) larvae of cotton aphids (*Aphis gossypii*) are released into each well, and 20 µL of the diluted solution C is sprayed into each well. Said well is defined as "treated group".

A well into which 20 µL of water containing a spreader (0.02% by volume) instead of the diluted solution C is sprayed is defined as "untreated group".

After the diluted solution C is dried, the upper part of the microplate is covered by a film sheet. After 5 days, the number of the surviving insects in each well is examined.

The controlling value is calculated by the following equation.

Controlling value(%)={1−(*Tai*)/(*Cai*)}×100 wherein the symbols in the equation represent the following meanings.

Cai: Number of the surviving insects at the time of the investigation in untreated group;

Tai: Number of the surviving insects at the time of the investigation in treated group Specific examples of the diluted solution C of which the effects can be confirmed in the Test Example 11 include the following 1) to 5).

1) A diluted solution C of any one combination described in the List A, wherein the concentration of the Present compound is 200 ppm and the concentration of the Present ingredient is 2,000 ppm. In the List A, Comp X represents any one compound selected from the Present compounds 1 to 9.

List A:
Comp X+clothianidin; Comp X+thiamethoxam; Comp X+imidacloprid; Comp X+thiacloprid; Comp X+flupyradifurone; Comp X+sulfoxaflor; Comp X+triflumezopyrim; Comp X+dicloromezotiaz; Comp X+beta-cyfluthrin; Comp X+tefluthrin; Comp X+fipronil; Comp X+chlorantraniliprole; Comp X+cyantraniliprole; Comp X+tetraniliprole; Comp X+thiodicarb; Comp X+carbofuran; Comp X+fluxametamide; Comp X+afoxolaner; Comp X+fluralaner; Comp X+broflanilide; Comp X+abamectin; Comp X+flupyram; Comp X+fluensulfone; Comp X+fluazaindolizine; Comp X+tioxazafen; Comp X+flupyrimin; Comp X+mycorrhizal fungi; Comp X+*Bradyrhizobium japonicum* TA-11; Comp X+*Bacillus firmus*; Comp X+*Bacillus firmus* 1-1582; Comp X+*Bacillus amyloliquefaciens*; Comp X+*Bacillus amyloliquefaciens* FZB42; Comp X+*Pasteuria nishizawae*; Comp X+*Pasteuria nishizawae* Pn1; Comp X+*Pasteuria penetrans*; Comp X+tebuconazole; Comp X+prothioconazole; Comp X+metconazole; Comp X+ipconazole; Comp X+triticonazole; Comp X+difenoconazole; Comp X+imazalil; Comp X+triadimenol; Comp X+tetraconazole; Comp X+flutriafol; Comp X+mandestrobin; Comp X+azoxystrobin; Comp X+pyraclostrobin; Comp X+trifloxystrobin; Comp X+fluoxastrobin; Comp X+picoxystrobin; Comp X+fenamidone; Comp X+metalaxyl; Comp X+metalaxyl-M; Comp X+fludioxonil; Comp X+sedaxane; Comp X+penflufen; Comp X+fluxapyroxad; Comp X+benzovindiflupyr; Comp X+boscalid; Comp X+carboxin; Comp X+penthiopyrad; Comp X+flutolanil; Comp X+captan; Comp X+thiram; Comp X+tolclofos-methyl; Comp X+thiabendazole; Comp X+ethaboxam; Comp X+mancozeb; Comp X+picarbutrazox; Comp X+oxathiapiprolin; Comp X+silthiofam; Comp X+inpyrfluxam.

2) A diluted solution C of any one combination described in the List A, wherein the concentration of the Present compound is 200 ppm and the concentration of the Present ingredient is 200 ppm.

3) A diluted solution C of any one combination described in the List A, wherein the concentration of the Present compound is 500 ppm and the concentration of the Present ingredient is 50 ppm.

4) A diluted solution C of any one combination described in the List A, wherein the concentration of the Present compound is 500 ppm and the concentration of the Present ingredient is 5 ppm.

5) A diluted solution C of any one combination described in the List A, wherein the concentration of the Present compound is 500 ppm and the concentration of the Present ingredient is 0.5 ppm.

Comparative Test Example 1

When the prescribed concentration was 125 ppm and the Present compound 1, 2, or 4, or a compound described in WO 2013/018928 pamphlet represented by the following formula (hereinafter referred to as "Comparative compound 1") was used as a test compound to carry out a test according to the Test method 8, each of the Present compound 1, 2, or 4 showed 100% as the mortality, while the Comparative compound 1 showed 10% as the mortality.

Comparative compound 1

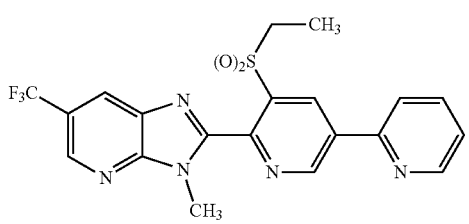

INDUSTRIAL APPLICABILITY

The Present compounds have excellent control effects on harmful arthropods.

The invention claimed is:

1. A compound represented by formula (I)

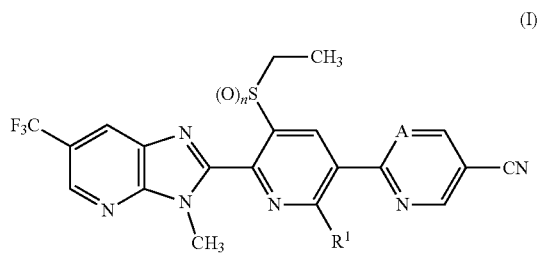

[wherein:

A represents a CH or a nitrogen atom;

$R^1$ represents a hydrogen atom or a $NR^2R^3$;

$R^2$ and $R^3$ are identical to or different from each other, and each represent a C1-C6 alkyl group optionally having one or more halogen atom(s) or a hydrogen atom; and n represents 0, 1, or 2].

2. The compound according to claim 1, wherein $R^1$ represents a hydrogen atom.

3. A composition for controlling a harmful arthropod comprising the compound according to claim 1 and an inert carrier.

4. A method for controlling a harmful arthropod which comprises applying an effective amount of the compound according to claim 1 to a harmful arthropod or a habitat where a harmful arthropod lives.

5. A composition comprising one or more ingredient(s) selected from the group consisting of Group (a) and Group (b), and the compound according to claim 1:

Group (a): a group consisting of insecticidal active ingredients, miticidal active ingredients, and nematicidal active ingredients;

Group (b): fungicidal active ingredients.

6. A method for controlling a harmful arthropod which comprises applying an effective amount of the composition according to claim 5 to a harmful arthropod or a habitat where a harmful arthropod lives.

7. A seed or a vegetative reproduction organ holding an effective amount of the compound according to claim 1.

8. A composition for controlling a harmful arthropod comprising the compound according to claim 2 and an inert carrier.

9. A method for controlling a harmful arthropod which comprises applying an effective amount of the compound according to claim 2 to a harmful arthropod or a habitat where a harmful arthropod lives.

10. A composition comprising one or more ingredient(s) selected from the group consisting of Group (a) and Group (b), and the compound according to claim 2:

Group (a): a group consisting of insecticidal active ingredients, miticidal active ingredients, and nematicidal active ingredients;

Group (b): fungicidal active ingredients.

11. A seed or a vegetative reproduction organ holding an effective amount of the compound according to claim 2.

12. A seed or a vegetative reproduction organ holding an effective amount of the composition according to claim 5.

* * * * *